US010595875B2

(12) United States Patent
Mayer et al.

(10) Patent No.: US 10,595,875 B2
(45) Date of Patent: Mar. 24, 2020

(54) DEVICE FOR RESTRICTING BLOOD FLOW TO ANEURYSMS

(71) Applicant: ENDOSTREAM MEDICAL LTD., Tel Aviv (IL)

(72) Inventors: Danel Mayer, Ramat Hasharon (IL); Alon May, Caesarea (IL)

(73) Assignee: ENDOSTREAM MEDICAL LTD., Tel Aviv (IL)

( * ) Notice: Subject to any disclaimer, the term of this patent is extended or adjusted under 35 U.S.C. 154(b) by 263 days.

(21) Appl. No.: 15/540,664

(22) PCT Filed: Dec. 31, 2015

(86) PCT No.: PCT/IL2015/051271
§ 371 (c)(1),
(2) Date: Jun. 29, 2017

(87) PCT Pub. No.: WO2016/108241
PCT Pub. Date: Jul. 7, 2016

(65) Prior Publication Data
US 2017/0367708 A1    Dec. 28, 2017

Related U.S. Application Data

(60) Provisional application No. 62/098,345, filed on Dec. 31, 2014, provisional application No. 62/216,412, filed on Sep. 10, 2015.

(51) Int. Cl.
*A61M 29/00* (2006.01)
*A61F 2/01* (2006.01)
(Continued)

(52) U.S. Cl.
CPC .... *A61B 17/12113* (2013.01); *A61B 17/1214* (2013.01); *A61B 17/12036* (2013.01);
(Continued)

(58) Field of Classification Search
CPC ...... A61F 2/01; A61F 2/013; A61F 2002/016; A61F 2002/011; A61B 17/12;
(Continued)

(56) References Cited

U.S. PATENT DOCUMENTS 5,350,397 A    9/1994    Palermo et al.
5,649,949 A    7/1997    Wallace et al.
(Continued)

FOREIGN PATENT DOCUMENTS

CN    202136073    2/2012
CN    203787320    8/2014
(Continued)

OTHER PUBLICATIONS

Written Opinion of PCT/IL2015/051271 Completed Apr. 19, 2016, dated Apr. 19, 2016 6 Pages.
(Continued)

*Primary Examiner* — Vi X Nguyen
(74) *Attorney, Agent, or Firm* — Sughrue Mion, PLLC

(57) ABSTRACT

A non-occlusive blood-restricting device is provided for use with a microcatheter and for treating a vascular malformation. The device includes a first section, a second section, and an intermediate section. The first section is configured to assume a first shape when deployed from the microcatheter within a portion of the vascular malformation so as to at least partially cover an orifice of the vascular malformation. The first shape defines a sequence of loops having a gradually decreasing diameter. The second section is configured to assume a second shape when deployed from the microcatheter, wherein the second shape defines a sequence of one or more loops having a constant or gradually decreasing diameter. The intermediate section connects the first and the second sections and is configured to space apart the first and
(Continued)

the second sections when deployed from the microcatheter. Other embodiments are also described.

19 Claims, 14 Drawing Sheets

(51) Int. Cl.
  *A61B 17/12* (2006.01)
  *A61B 17/22* (2006.01)
  *A61B 17/00* (2006.01)
(52) U.S. Cl.
  CPC .. *A61B 17/12145* (2013.01); *A61B 17/12172* (2013.01); *A61B 2017/00526* (2013.01); *A61B 2017/22042* (2013.01); *A61F 2002/016* (2013.01)
(58) Field of Classification Search
  CPC .......... A61B 17/12036; A61B 17/1214; A61B 17/12113; A61M 29/00
  See application file for complete search history.

(56) References Cited

U.S. PATENT DOCUMENTS

| | | | |
|---|---|---|---|
| 5,749,891 A | 5/1998 | Ken et al. |
| 5,935,148 A | 8/1999 | Villar et al. |
| 6,036,720 A | 4/2000 | Abrams et al. |
| 6,306,141 B1 | 10/2001 | Jervis |
| 6,338,736 B1 | 1/2002 | Boosfeld et al. |
| 6,371,972 B1 | 4/2002 | Wallace et al. |
| 6,383,174 B1 | 5/2002 | Eder |
| 6,506,204 B2 | 1/2003 | Mazzocchi |
| 6,551,305 B2 | 4/2003 | Ferrera et al. |
| 6,740,096 B2 | 5/2004 | Teague et al. |
| 6,790,218 B2 | 9/2004 | Jayaraman |
| 7,128,736 B1 | 10/2006 | Abrams et al. |
| 7,229,461 B2 | 1/2007 | Chin et al. |
| 7,323,000 B2 | 1/2008 | Monstdt et al. |
| 7,377,932 B2 | 5/2008 | Mitelberg et al. |
| 7,569,066 B2 | 8/2009 | Gerberding et al. |
| 8,007,509 B2 | 8/2011 | Buiser |
| 8,333,796 B2 | 12/2012 | Tompkins et al. |
| 8,444,667 B2 | 5/2013 | Porter |
| 8,518,064 B2 | 8/2013 | Kurrus et al. |
| 8,570,343 B2 | 10/2013 | Halstead |
| 8,747,454 B2 | 6/2014 | Khairkhahan et al. |
| 8,764,772 B2 | 7/2014 | Tekulve |
| 8,906,057 B2 | 12/2014 | Connor et al. |
| 9,138,232 B2 | 9/2015 | Connor |
| 9,629,635 B2 | 4/2017 | Hewitt et al. |
| 2002/0049468 A1 | 4/2002 | Streeter et al. |
| 2002/0169473 A1 | 11/2002 | Sepetka et al. |
| 2003/0055451 A1 | 3/2003 | Jones et al. |
| 2003/0216772 A1 | 11/2003 | Konya et al. |
| 2004/0034386 A1 | 2/2004 | Fulton et al. |
| 2004/0098027 A1 | 5/2004 | Teoh et al. |
| 2004/0167597 A1 | 8/2004 | Costantino et al. |
| 2005/0038460 A1 | 2/2005 | Jayaraman |
| 2005/0107823 A1* | 5/2005 | Leone .............. A61B 17/12022 606/200 |
| 2006/0155323 A1 | 7/2006 | Porter et al. |
| 2006/0206199 A1 | 9/2006 | Churchwell et al. |
| 2007/0123928 A1 | 5/2007 | Farnan |
| 2007/0150045 A1 | 6/2007 | Ferrera |
| 2008/0114436 A1 | 5/2008 | Dieck et al. |
| 2008/0300616 A1 | 12/2008 | Que et al. |
| 2009/0099647 A1 | 4/2009 | Glimsdale et al. |
| 2009/0216265 A1 | 8/2009 | DeVries et al. |
| 2010/0121350 A1 | 5/2010 | Mirigian |
| 2011/0022149 A1 | 1/2011 | Cox et al. |
| 2012/0071911 A1 | 3/2012 | Sadasivan et al. |
| 2012/0143237 A1 | 6/2012 | Cam et al. |
| 2014/0180377 A1 | 6/2014 | Bose et al. |
| 2017/0135701 A1 | 5/2017 | Beckham et al. |
| 2017/0150971 A1 | 6/2017 | Hines |
| 2017/0333678 A1 | 11/2017 | Bowman et al. |

FOREIGN PATENT DOCUMENTS

| | | |
|---|---|---|
| WO | 2012/158883 A1 | 11/2012 |
| WO | 2014165256 | 10/2014 |

OTHER PUBLICATIONS

International Search of PCT/IL2015/051271 Completed Apr. 19, 2016, dated Apr. 19, 2016 5 Pages.
Nit-Occlud PDA, pfm medical (Jun. 2012).
Medtronic EV3 Axium Youtube excerpts downloaded Aug. 13 2018.
An International Search Report and a Written Opinion both dated Oct. 3, 2017, which issued during the prosecution of Applicant's PCT/IL2017/050694.
An extended European Search Report issued in European Appl. No. 17814898.7, dated Feb. 3, 2020.

* cited by examiner

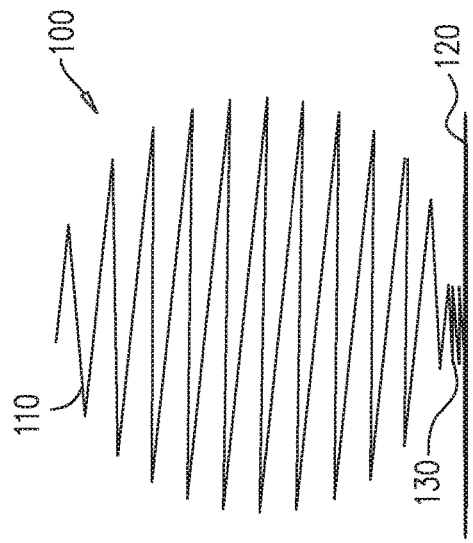
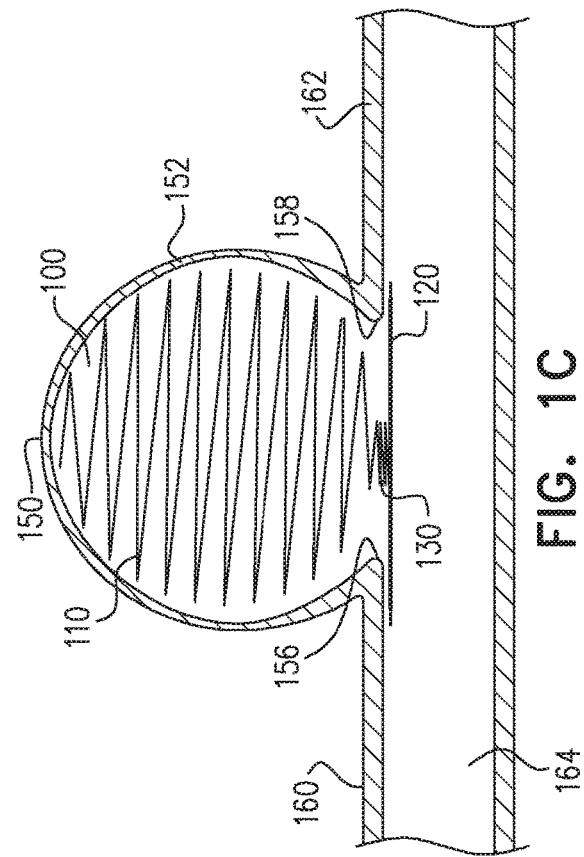
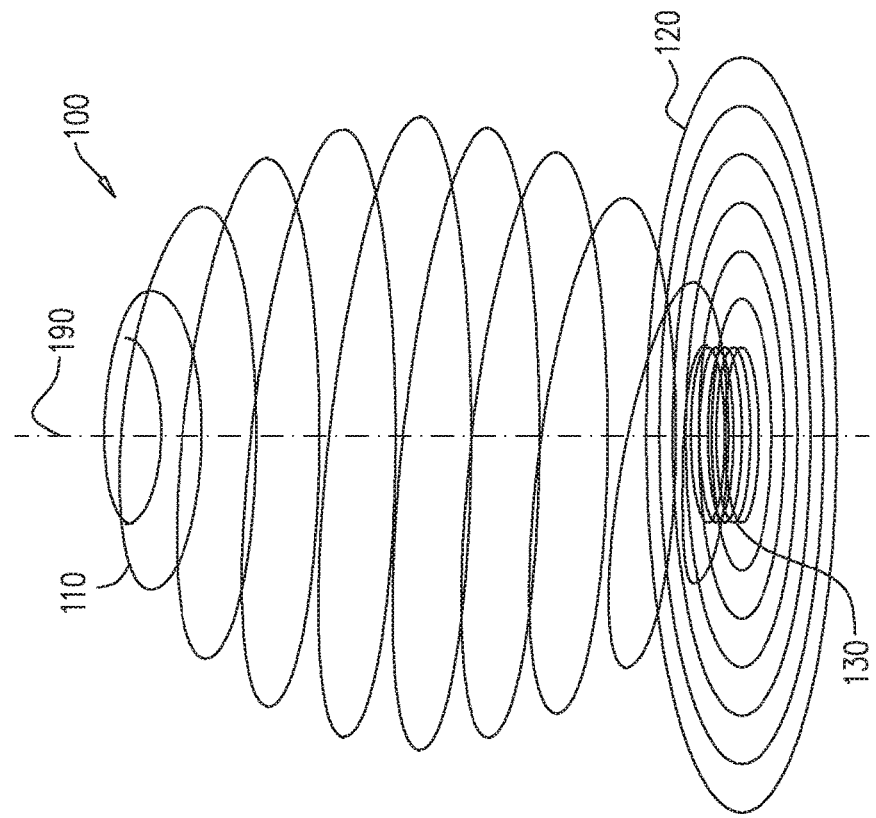

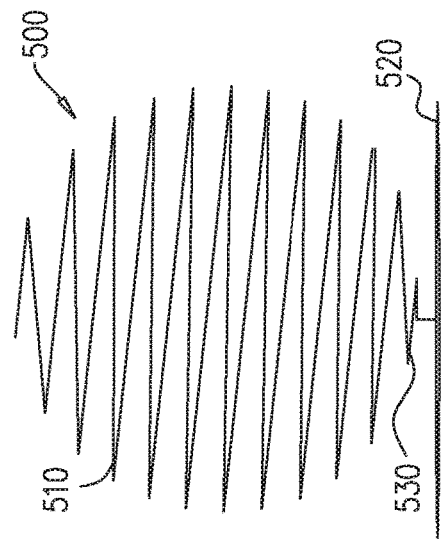
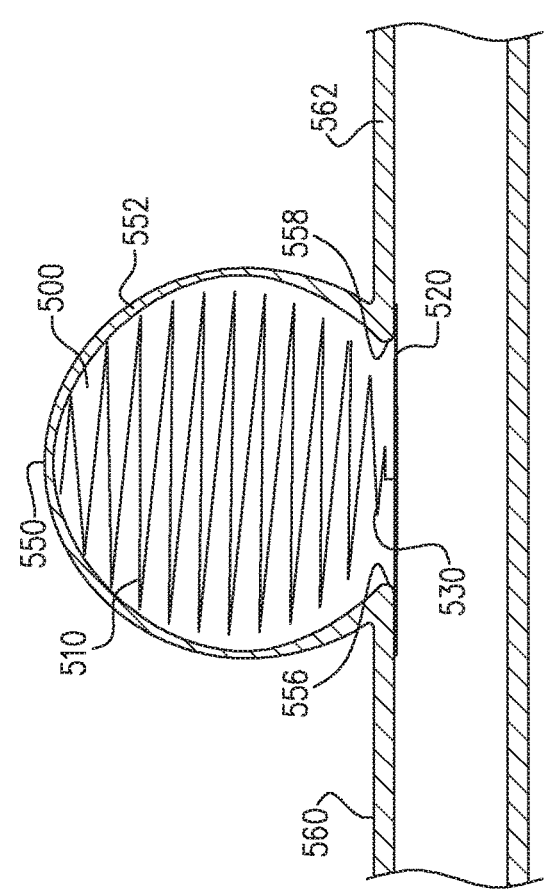
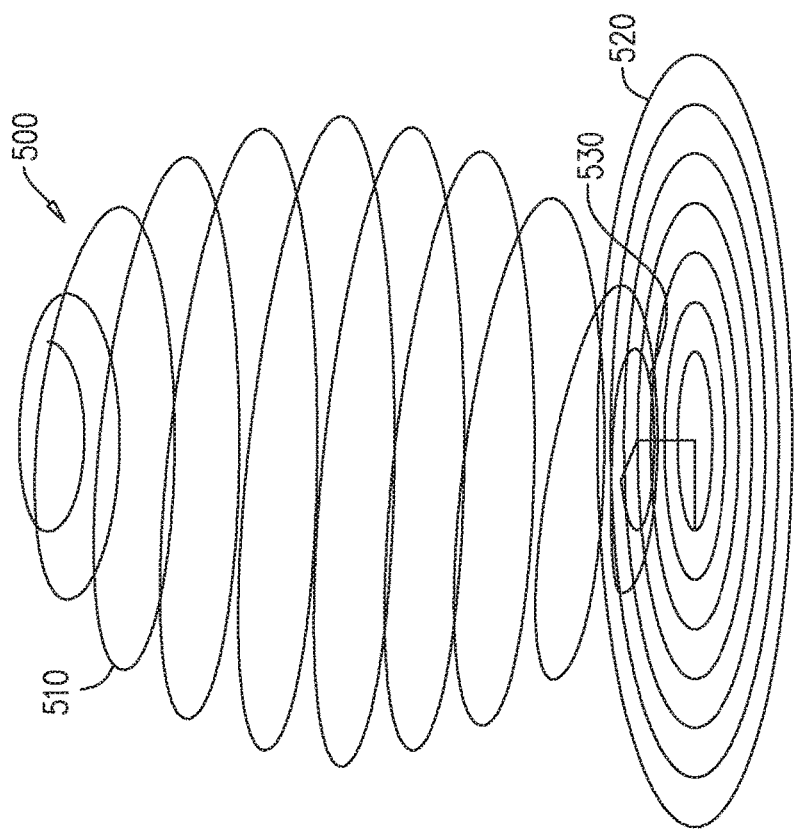
FIG. 5B
FIG. 5C
FIG. 5A

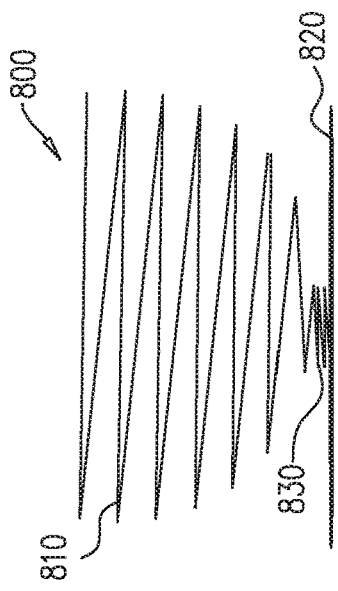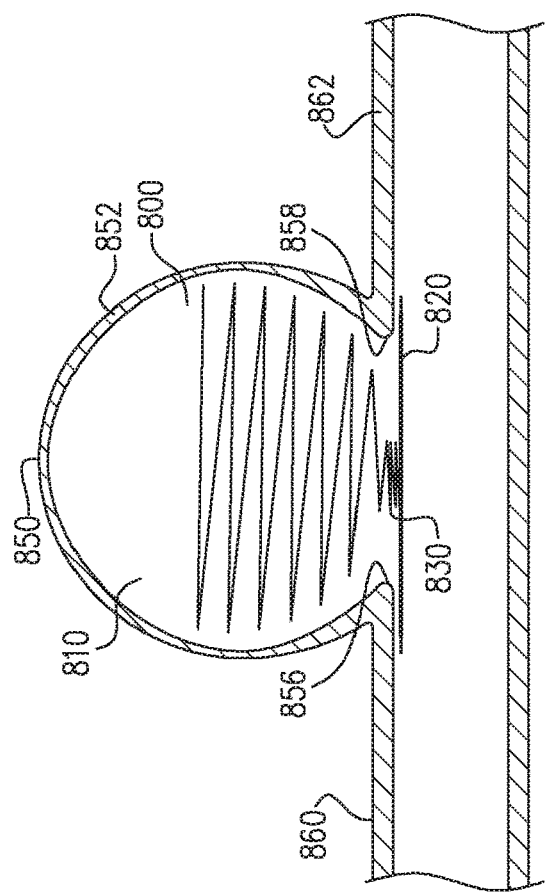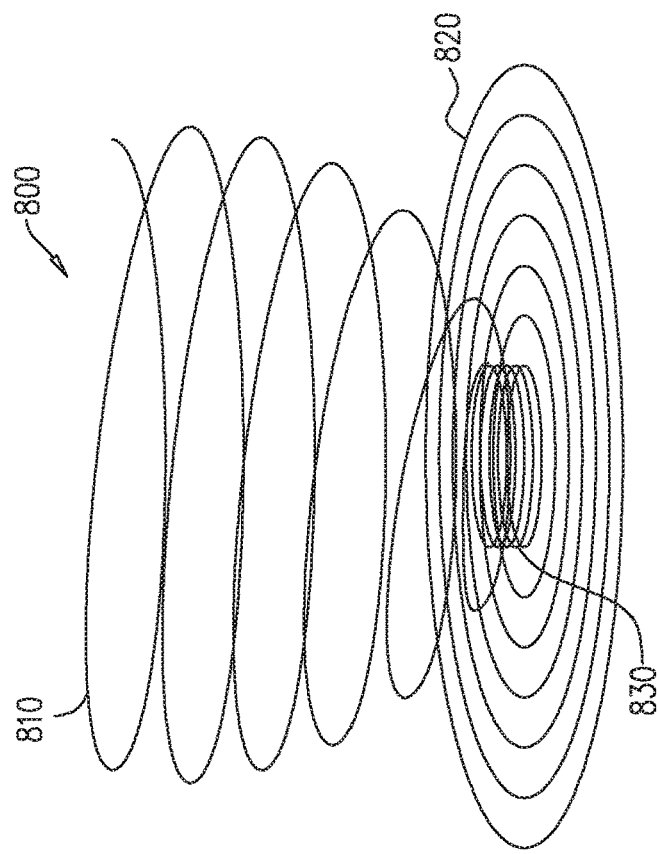

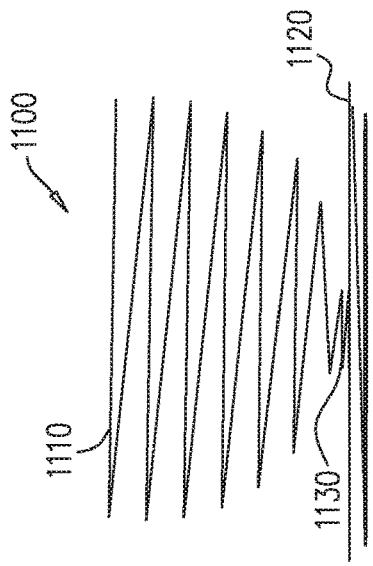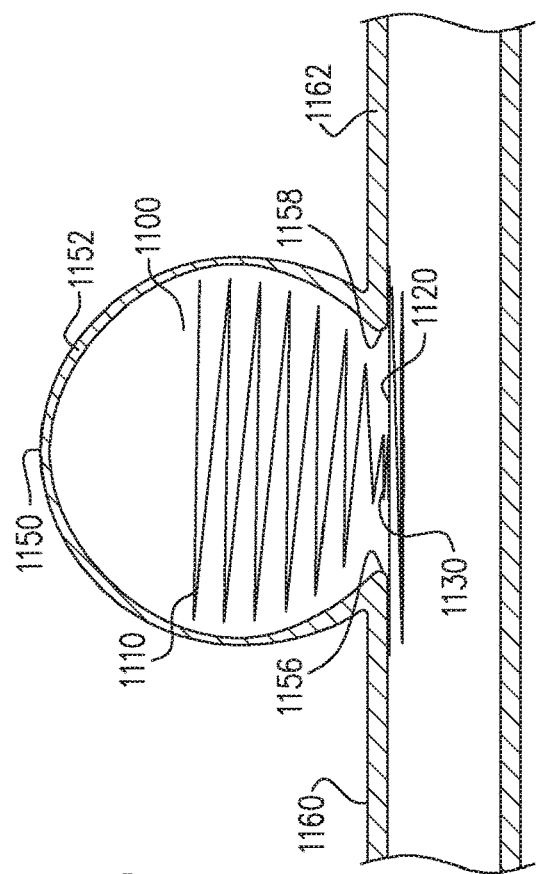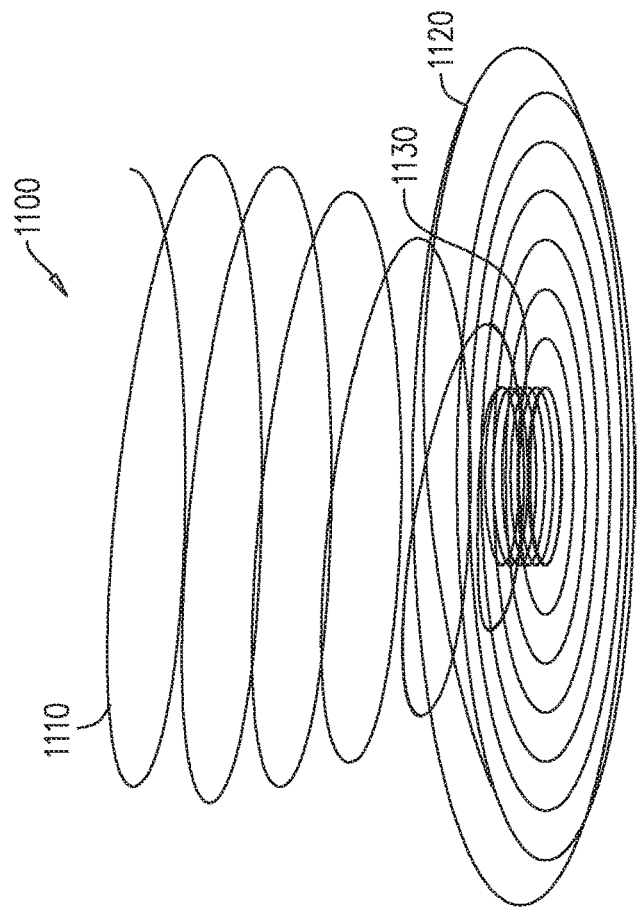

DEVICE FOR RESTRICTING BLOOD FLOW TO ANEURYSMS

TECHNICAL FIELD

The present disclosure generally relates to the field of aneurysms and restriction of blood flow thereto.

BACKGROUND

An aneurysm is an abnormal local dilation of an artery caused by a weakening of the artery wall. In the past, cerebral aneurysms were frequently treated by direct surgical intervention. For example, by installing a clip around the base of the aneurysm to prevent passage of blood between the aneurysm and the lumen of the vessel. Attempts have then been made to develop minimally invasive techniques for treating such aneurysms, for example, by filling the aneurysm with coils, such that the aneurysm eventually becomes a solid mass of coils and thrombus.

SUMMARY

The present disclosure relates to a device and methods for treating vascular malformations, such as aneurysms.

Advantageously, the device disclosed herein, includes a distal end, which, due to its coil (spiral) formed configuration, is configured to restrict flow into the aneurysm without completely occluding the orifice thereof. This fosters gradual healing of the aneurysm as blood flow is altered, both in direction and speed, and facilitates gradual coagulation of blood within the sac. The configuration of the distal end may also reduce intra-operative ruptures in comparison to standard coiling, since it does not impose direct pressure on the delicate aneurysm dome. As a further advantage, the device disclosed herein is configured to treat the aneurysm neck (rather than the sac as in the case of coils, or the parent vessel, like in the case of stents), albeit without requiring open-surgery, as in the case of clipping. Furthermore, whereas aneurysm recanalization happens in about 30% of aneurysms treated by filling the aneurysm with coils, the device disclosed herein restricts the flow of blood at the neck of the aneurysm, thereby minimizing the risk of aneurysm regrowth due to neck remnants.

In addition, the device disclosed herein is formed of a single looped wire having a proximal end (within the parent vessel) a distal end (within the aneurysm sac) and optionally an intermediate section (positioned along the neck of the aneurysm) interconnecting the proximal and distal ends. By being formed of a single looped wire, the deployment of the device within the blood vessel and its malformation is simplified as it implicates implanting only a single device. Moreover, by having both an intrasaccular section and an intraluminal section, the device is firmly secured on both sides of the aneurysm, thereby essentially eliminating the risk of detachment of the device downstream.

Additionally, the distal, intrasaccular end of the device is designed to follow the shape of an aneurysm sac so as to line the distal end of the device to the wall of the aneurysm sac, while avoiding excess pressure on the aneurysm sac, which is susceptible to rupture. Due to lining within the aneurysm sac, the proximal end of the device needs only a minimal overlap with the vessel wall, thereby significantly reducing the risk of blocking neighboring blood vessels that arise from the same parent vessel as the aneurysm (i.e. perforator arteries such as lenticulostriate arteries adjacent cerebral aneurysms), a risk common to stent placement procedures.

The minimal coverage of healthy tissue may further obviate, or at least reduce, the need for anti-platelet therapy, frequently required during stenting to minimize aggregation of platelets and ultimately thrombus formation in the parent vessel.

As an additional advantage, the proximal end of the device is designed to be minimally protruding into the lumen of the parent vessel, and may therefore serve as a scaffold for tissue growth along the inner edge of the neck and along the adjacent normal vessel wall, thereby promoting development of a normal lining and closure of the aneurysm.

According to some embodiments, there is provided herein a non-occlusive blood restricting device for treating a vascular malformation, the blood restricting device consisting of a wire comprising: a first section configured to be coiled into a first coil when deployed within the vascular malformation; wherein the first coil comprises a spiral or sequence of loops, the spiral or sequence of loops having a gradually decreasing diameter; and wherein the first coil is configured to line a neck and/or a wall of the vascular malformation so as to at least partially cover an orifice thereof; and a second section configured to be deployed within a blood vessel, adjacent the vascular malformation; wherein the second section is configured to form a second coil, circumferentially lining a wall of the blood vessel.

According to some embodiments, there is provided herein a kit for treating a vascular malformation, the kit comprising: a non-occlusive blood restricting device for treating a vascular malformation, the blood restricting device consisting of a wire comprising: a first section configured to be coiled into a first coil when deployed within the vascular malformation; wherein the first coil comprises a spiral or sequence of loops, said spiral or sequence of loops having a gradually decreasing diameter; and wherein said first coil is configured to line a neck and/or a wall of the vascular malformation so as to at least partially cover an orifice thereof; and a second section configured to be deployed within a blood vessel, adjacent the vascular malformation; wherein the second section is configured to form a second coil, circumferentially lining a wall of the blood vessel; and a microcatheter configured to deliver the non-occlusive blood restricting device to a target area.

According to some embodiments the terms "catheter" and "microcatheter" may be used interchangeably.

According to some embodiments, there is provided herein a method for treating a vascular malformation, the method comprising: providing a non-occlusive blood restricting device for treating a vascular malformation, the blood restricting device consisting of a wire comprising: a first section configured to be coiled into a first coil when deployed within the vascular malformation; wherein the first coil comprises a spiral or sequence of loops, the spiral or sequence of loops having a gradually decreasing diameter; and wherein the first coil is configured to line a neck and/or a wall of the vascular malformation so as to at least partially cover an orifice thereof; and a second section configured to be deployed within a blood vessel, adjacent the vascular malformation; wherein the second section is configured to form a second coil, circumferentially lining a wall of the blood vessel, inserting, using a microcatheter, the non-occlusive blood restricting device into the blood vessel; deploying the first section within the vascular malformation; and deploying the second section within the blood vessel. According to some embodiments, in cases wherein at least a part of the wire forms a spring (coil) defining a primary wind, wherein the first and/or second sections of said wire define secondary winds and wherein the device further comprising an auxiliary wire disposed along at least a part of the length of the wire, the method further may further include removing the auxiliary wire after or during the deployment. According to some embodiments, in cases wherein at least a part of the wire is a tube and wherein the device further comprising an auxiliary wire disposed along at least a part of the length of the wire, the method further may further include removing the auxiliary wire after or during the deployment.

According to some embodiments, the first section may be essentially parallel to the second section, when not restrained. According to some embodiments, a central axis of the first section may be essentially parallel to a central axis of the second section, when not restrained.

According to some embodiments, the first section may be essentially perpendicular to the second section, when not restrained. According to some embodiments, a central axis of the first section may be essentially perpendicular to a central axis of the second section, when not restrained.

According to some embodiments, an angle of about 20°-30° is formed between the first section and the second section, when not restrained. According to some embodiments, an angle of about 20°-30° is formed between a central axis of the first section and a central axis of the second section, when not restrained. According to some embodiments, an angle of about 30°-45° is formed between the first section and the second section, when not restrained. According to some embodiments, an angle of about 30°-45° is formed between a central axis of the first section and a central axis of the second section, when not restrained. According to some embodiments, an angle of about 45°-60° is formed between the first section and the second section, when not restrained. According to some embodiments, an angle of about 45°-60° is formed between a central axis of the first section and a central axis of the second section, when not restrained. According to some embodiments, an angle of about 60°-90° is formed between the first section and the second section, when not restrained. According to some embodiments, an angle of about 60°-90° is formed between a central axis of the first section and a central axis of the second section, when not restrained.

According to some embodiments, the term "not restrained" may refer to the device's configuration when no external force is applied on the device. Such external force may include, for example, a force applied by a catheter or a blood vessel.

According to some embodiments, the device may further include an intermediate section, the intermediate section spacing apart the first and second spirals. According to some embodiments, the intermediate section forms tension force between the first and second spirals. According to some embodiments, the tension force between the first and second spirals may be determined by the design and/or characteristics of the intermediate section forms.

According to some embodiments, the first and the second sections are parts of a single wire. According to some embodiments, the first coil has a form of a bowl when deployed and/or when not restrained. According to some embodiments, the first coil has a form of a flat plate, when deployed and/or when not restrained. According to some embodiments, the first and second sections are made of a memory shape alloy. According to some embodiments, the first and second sections are made of a super elastic alloy.

According to some embodiments, the distal end of the first section forms an outermost loop of the first coil and a proximal end of the first section forms an innermost loop of the first coil.

According to some embodiments, a force exerted by the first section on a catheter configured to deliver the device to the blood vessel is gradually changing along a length of the first section. According to some embodiments, the force exerted on the catheter by a distal end of the first section is weaker than the force exerted on the catheter by a proximal part of the first section. According to some embodiments, the force exerted on the catheter by a distal end of the first section is stronger than the force exerted on the catheter by a proximal part of the first section. According to some embodiments, the diameter of the wire at a distal end of the first section is smaller than a diameter of the wire at a proximal part of the first section, such that the wire has a tapered shape at the first section thereof. According to some embodiments, the diameter of the wire at a distal end of the first section is larger than a diameter of the wire at a proximal part of the first section, such that the wire has a tapered shape at the first section thereof. According to some embodiments, the wire is a tube. According to some embodiments, the tube comprises a plurality of cuts along at least a part of the first section thereof. According to some embodiments, a distance between said plurality of cuts varies. According to some embodiments, a distance between the plurality of cuts varies such that the tube has a variable pitch along the first section thereof. According to some embodiments, the tube has a variable pitch along the first section thereof. According to some embodiments, the tube has a variable flexibility along the first section thereof.

According to some embodiments, the tube has a variable flexibility. According to some embodiments, the wire has a variable flexibility.

According to some embodiments, the first coil comprises an aperture essentially in a center thereof, the aperture is configured to at least partially line the orifice of the vascular malformation.

According to some embodiments, at least a part of the wire is a spring defining a primary wind wherein the first and the second sections of the wire define secondary winds. According to some embodiments, the device further includes a core wire threaded in a proximal part of the first section. According to some embodiments, the core wire is tapered having a smaller diameter at a distal end thereof compared to a diameter at a proximal part thereof. According to some embodiments, the device further includes an auxiliary wire threaded along at least a part of the length of the wire, the auxiliary wire is configured to facilitate the deployment of the device in the blood vessel and to be removed after or during the deployment. According to some embodiments, the auxiliary wire is disposed along the length of the first section. According to some embodiments, the auxiliary wire is disposed along the length of the second section. According to some embodiments, the auxiliary wire is disposed along the length of the intermediate section.

According to some embodiments, there is provided a non-occlusive device for treating a vascular malformation in a blood vessel, the device having a first spiral section deployable within the vascular malformation and configured to line a wall thereof, a second spiral section deployable within the vessel so as to at least partially cover an orifice of the vascular malformation, and an intermediate section connecting the first and second spiral sections and positionable within a neck of the vascular malformation.

According to some embodiments, the device may be configured to facilitate a restricted flow of blood into the vascular malformation.

According to some embodiments, the first and second spiral sections and the intermediate section may be segments of a single wire.

According to some embodiments, the intermediate section may be coil formed. According to some embodiments, the second spiral section may have a form of a bowl.

According to some embodiments, the first spiral section may be configured to line the wall of the vascular malformation along a circumference thereof.

According to some embodiments, when the device is deployed within the blood vessel, the intermediate section exerts a compression force on the second spiral section, thereby anchoring the second spiral section to a wall of the blood vessel.

According to some embodiments, the device may include a memory shape alloy. According to some embodiments, the device may include a drug eluting material.

According to some embodiments, the device may be at least partially radiopaque. According to some embodiments, the device may be deliverable by a microcatheter.

According to some embodiments, the aneurysm may be a cerebral aneurysm.

According to some embodiments, there is provided a method of treating a vascular malformation in a blood vessel of a subject, the method including: introducing into the blood vessel a microcatheter comprising a non-occlusive device, the non-occlusive device having a first spiral section; a second spiral section, and an intermediate section connecting the first and second spiral sections, and deploying the non-occlusive device.

According to some embodiments, deploying the device may include deploying the first spiral section of the device within the vascular malformation so as to engage a wall of the vascular malformation along a circumference thereof, and deploying the second spiral section of the device within the blood vessel such that it at least partially covers an orifice of the vascular malformation. According to some embodiments, the first spiral section may initially be deployed within the vascular malformation followed by deployment of the second spiral section within the blood vessel.

According to some embodiments, the method may further include releasing the non-occlusive device from the microcatheter. According to some embodiments, the method may further include clinching the first and second spiral sections to the vessel wall at opposite sides thereof.

According to some embodiments, the method may include altering a direction and/or a speed of blood flow into the vascular malformation. According to some embodiments, the method may facilitate a restricted flow of blood into the vascular malformation.

According to some embodiments, the vascular malformation may be an aneurysm. According to some embodiments, the aneurysm is a cerebral aneurysm.

According to some embodiments, there is provided a system for treating a vascular malformation in a blood vessel. According to some embodiments the system may include a non-occlusive device and a microcatheter.

According to some embodiments, the non-occlusive device may include a first spiral section deployable within the vascular malformation and configured to line a wall thereof; a second spiral section deployable within the vessel so as to at least partially cover an orifice of the vascular malformation, and an intermediate section connecting the first and second spiral sections and positionable within a neck of the vascular malformation.

According to some embodiments, the device may be configured to facilitate a restricted flow of blood into the vascular malformation.

According to some embodiments, the second spiral section may be configured to alter a direction and/or a speed of blood flow there through, According to some embodiments, the microcatheter may be configured to deliver the non-occulsive device to the vascular malformation.

According to some embodiments, there is provided a blood restricting device for treating a vascular malformation in a blood vessel, the blood restricting device having a first section configured to obtain a spiral form when deployed within the vascular malformation. In its spiral form, the first section is configured to line the neck of the vascular malformation so as to at least partially cover an orifice of the vascular malformation. According to some embodiments, the first section may be configured to alter a direction and/or a speed of blood flow through the vascular malformation. The blood restricting device further includes a second section configured to be deployed within the vessel, adjacent the vascular malformation. According to some embodiments, the second section is configured to form a spiral circumferentially lining the wall of the blood vessel along a predetermined length thereof. According to some embodiments, the second section is configured to form one or more loops (e.g. a single loop), within the blood vessel. According to some embodiments, the one or more loops circumferentially line the wall of the blood vessel. According to some embodiments, the one or more loops may be located at a position within the blood vessel essentially in front of the vascular malformation.

According to some embodiments, the first section is essentially perpendicular to the second section when deployed. According to some embodiments, the first section is angled relative to the second section when deployed.

According to some embodiments, the blood restricting device further includes an intermediate section interconnecting the first and second sections.

According to some embodiments, the first, second and optionally intermediate sections may be segments of a single wire.

According to some embodiments, the first section may have a form of a bowl when deployed in the vascular malformation. According to some embodiments, the first section may have a form of a looped flat plate when deployed in the vascular malformation.

According to some embodiments, when the blood restricting device is deployed within the blood vessel, the second section and/or the intermediate section, exerts a compression force on the first section, thereby anchoring the first section to the neck of the vascular malformation.

According to some embodiments, the blood restricting device may include a memory shape alloy. According to some embodiments, the blood restricting device may be made of a memory shape alloy. According to some embodiments, the blood restricting device may include a drug eluting material.

According to some embodiments, the blood restricting device may be at least partially radiopaque. According to some embodiments, the blood restricting device may be deliverable by a microcatheter.

According to some embodiments, the aneurysm may be a cerebral aneurysm.

According to some embodiments, there is provided a method of treating a vascular malformation in a blood vessel of a subject, the method including: introducing into the blood vessel a microcatheter comprising a blood restricting device having a first section and a second section; deploying the first section of the device within the vascular malformation, wherein deploying the first section comprises forming a spiral and/or a loop from the first section, the spiral and/or loop lining the neck of the vascular malformation so as to at least partially cover the orifice of the vascular malformation, deploying the second section within the blood vessel adjacent the to the vascular malformation. According to some embodiments, deploying the second section comprises forming a spiral from the second section, the spiral circumferentially lining the wall of the blood vessel along a predetermined length thereof. According to some embodiments, deploying the second section comprises forming one or more loops (e.g. a single loop) from the second section, the one or more loops circumferentially lining the wall of the blood vessel. According to some embodiments, the one or more loops may be located at a position within the blood vessel essentially in front of the vascular malformation.

According to some embodiments, the first section may be configured to line the neck of the vascular malformation so as to at least partially cover an orifice of the vascular malformation.

According to some embodiments, deploying the blood restricting device may include deploying the first section of the device within the vascular malformation, and deploying the second section of the device within the blood vessel. According to some embodiments, the first section may initially be deployed within the vascular malformation followed by deployment of the second section within the blood vessel. According to some embodiments, the deployment of the first sections within the vascular malformation may be simultaneous with the deployment of the second section within the blood vessel.

According to some embodiments, the method may further include releasing the blood restricting device from the microcatheter.

According to some embodiments, the method may include altering a direction and/or a speed of blood flow into the vascular malformation. According to some embodiments, the method may facilitate a restricted flow of blood into the vascular malformation.

According to some embodiments, the vascular malformation may be an aneurysm. According to some embodiments, the aneurysm is a cerebral aneurysm.

According to some embodiments, there is provided a system for treating a vascular malformation in a blood vessel. According to some embodiments the system may include a blood restricting device and a microcatheter.

According to some embodiments, the blood restricting device may include a first section configured to obtain a spiral and/or loop form when deployed within the vascular malformation. In its spiral and/or loop form, the first section is configured to line the neck of the vascular malformation so as to at least partially cover an orifice of the vascular malformation, and a second section configured to be deployed within the vessel, adjacent the vascular malformation. According to some embodiments, the second section is configured to form a spiral circumferentially lining the wall of the blood vessel along a predetermined length thereof. According to some embodiments, the second section is configured to form one or more loops (e.g. a single loop), within the blood vessel. According to some embodiments, the one or more loops circumferentially line the wall of the blood vessel. According to some embodiments, the one or more loops may be located at a position within the blood vessel essentially in front of the vascular malformation.

According to some embodiments, the first section is essentially perpendicular to the second section when deployed. According to some embodiments, the first section is angled relative to the second section when deployed.

According to some embodiments, the first section may have a form of a bowl when deployed in the vascular malformation. According to some embodiments, the first section may have a form of a looped flat plate when deployed in the vascular malformation.

According to some embodiments, the blood restricting device further includes an intermediate section interconnecting the first and second sections.

According to some embodiments, the device may be configured to facilitate a restricted flow of blood into the vascular malformation.

According to some embodiments, the first section may be configured to alter a direction and/or a speed of blood flow there through, According to some embodiments, the microcatheter may be configured to deliver the blood restricting device to the vascular malformation.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

FIG. 1A-FIG. 1B schematically illustrates a non-occlusive device for treating vascular malformations, according to some embodiments;

FIG. 1C schematically illustrates the non-occlusive device of FIG. 1A and FIG. 1B, deployed within a vascular malformation, according to some embodiments;

FIG. 5A-FIG. 5B schematically illustrates a non-occlusive device for treating vascular malformations, according to some embodiments;

FIG. 5C schematically illustrates the non-occlusive device of FIG. 5A and FIG. 5B, deployed within a vascular malformation, according to some embodiments;

FIG. 8A-FIG. 8B schematically illustrates a non-occlusive device for treating vascular malformations, according to some embodiments;

FIG. 8C schematically illustrates the non-occlusive device of FIG. 8A and FIG. 8B, deployed within a vascular malformation, according to some embodiments;

FIG. 11A-FIG. 11B schematically illustrates a non-occlusive device for treating vascular malformations, according to some embodiments;

FIG. 11C schematically illustrates the non-occlusive device of FIG. 11A and FIG. 11B, deployed within a vascular malformation, according to some embodiments;

DETAILED DESCRIPTION

Figure 2B:
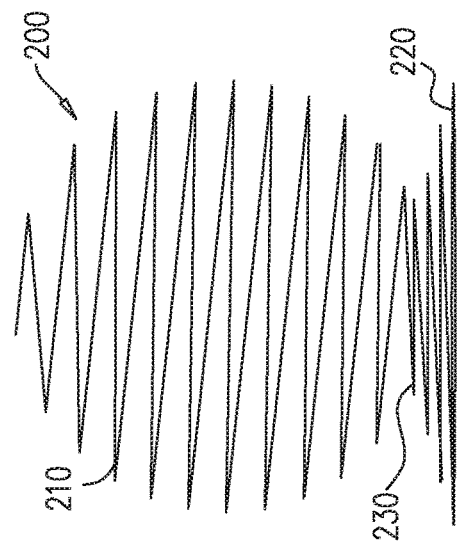
FIG. 2A-FIG. 2B schematically illustrates a non-occlusive device for treating vascular malformations, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

There is provided, according to some embodiments, a device for treating vascular malformations in blood vessels, the device including a wire having a first and a second section. The first section is configured to coil into a first coil when deployed within the vascular malformation, the coil including a spiral or sequence of rings having a gradually decreasing diameter. The first coil is configured to line a neck and/or a wall of the vascular malformation so as to at least partially cover an orifice thereof. The first section, which is configured to coil into a first coil, may also be referred to as a distal section. The second section is configured to form a second coil when deployed. The second coil is configured to be deployed within the blood vessel, adjacent the vascular malformation and to circumferentially line a wall of the blood vessel. The second section, which is configured to form a second coil, may also be referred to as a proximal section. It is thus understood that the device for treating vascular malformations in blood vessels may be formed of a single wire, which folds into at least a first and a second coil. Such configuration enables the delivery of the device through a catheter having an internal diameter of below 0.69 millimeters. This is in contrast to occlusion devices such as cage type structures, which include separate collapsed elements, which are expanded upon deployment. It is noted that although the diameters provided hereinabove are typically suitable for neurovasculature, other sizes/diameters that may be used for any other endo vascular application are also covered under the scope of this disclosure.

As used herein the term "vascular deformation" and "vascular malformation" may be used interchangeably and may refer to any congenital and/or non-congenital blood vessel abnormality, such as, but not limited to, aneurysms, fistulas, tumors and arteriovenous malformations. Each possibility is a separate embodiment. Aneurysms are a result of a weakened blood vessel wall, and can be a result of a hereditary condition or an acquired disease. If left untreated, an aneurysm can rupture, leading to life threatening situations. For example, a ruptured aneurysm may cause intracranial hemorrhage, which can result in death or severe neurologic deficit. In some patients, aneurysms can put pressure on nerves or brain tissue, causing pain, abnormal sensations, and/or seizures.

According to some embodiments, the aneurysm may be a saccular aneurysm formed in the wall of blood vessels, most typically arteries. The aneurysm may be described as a blood-filled balloon-like sac having a neck, which leads into the parental vessel. While aneurysms can occur in any blood vessel of the body, a large percentage of aneurysms are found in cerebral arteries. Thus, according to some embodiments, the aneurysm may be a cerebral aneurysm, such as, but not limited to, berry aneurysms, wide-neck aneurysms, giant aneurysms, dissecting aneurysms and fusiform aneurysms. Each possibility is a separate embodiment. Additional non-limiting examples of aneurysms include coronary artery aneurysms, ventricular aneurysms, aneurysm of sinus of Valsalva, and aneurysms following cardiac surgery, aortic aneurysms including thoracic aortic aneurysms and abdominal aortic aneurysms, intraparechymal aneurysms and capillary aneurysms. Each possibility is a separate embodiment. According to some embodiments, the aneurysm may be an aneurysm formed at or near a bifurcation, where a main vessel branches into two or more separate vessels. Aneurysms, at or near bifurcations, present unique challenges to successful treatment.

According to some embodiments, the device, disclosed herein, may be non-occlusive. According to some embodiments, the device may be a blood restricting device. As used herein the term "non-occlusive device" may refer to a device which alters the flow of blood into the aneurysm but which does not necessarily impede blood flow into the malformation. According to some embodiments, the non-occlusive device may be a flow-altering device. According to some embodiments, the device is configured to restrict flow into the aneurysm. According to some embodiments, the device is configured to facilitate a restricted flow of blood into the vascular malformation. According to some embodiments, the term "restricted flow" may refer to a flow of blood altered in its direction, pressure or speed. According to some embodiment, a restricted flow of blood may refer to a flow of blood being reduced by 10%-50%, 50%-60%, 50%-70%, 80%, 90% or more as compared to the flow of blood into the untreated aneurysm. Each possibility is a separate embodiment. According to some embodiments, at least 10%, 20%, 30%, 40% or more of the pre-treatment blood flow into the aneurysm is maintained after treatment. Each possibility is a separate embodiment.

According to some embodiments, the device may be a stand-alone device. That is, the device alone may be sufficient for treatment of aneurysms. However, according to some alternative embodiments, the device may be used in conjunction with standard coils, such as, but not limited to, Guglielmi detachable coils (GDC). According to some embodiments, the device may be suitable for minimally invasive treatments of aneurysms. According to some embodiments, the device may be configured to support and/or be anchored to the aneurysm sac. According to some embodiments, the device may be configured to support and/or be anchored to the aneurysm neck and/or to the wall of the parent blood vessel. According to some embodiments, the device is configured to support and/or be anchored to the aneurysm sac and to facilitate a restricted blood flow into the aneurysm.

According to some embodiments, the first section may be a distal end of the wire. As used herein, the term "distal end" may refer to the end of the wire, which is the first to exit the micro catheter with which it is delivered and/or the end of the wire, which is first introduced to the aneurysm sac, when in use.

According to some embodiments, the second section may be a proximal end of the wire. As used herein, the term "proximal end" may refer to the end of the wire, which is the last to exit the micro catheter with which it is delivered. Additionally or alternatively the proximal end of the wire may be part of the wire positionable within/along the lumen of the parent blood vessel.

As used herein the term "coil formed" may refer to a sequence or spiral of rings having a gradually decreasing diameter. It is thus understood that the device, disclosed herein, may be formed of a (single) wire having a first coilable section at an end thereof configured to enter and line at least part of the aneurysm sac and a second coilable section proximal to the first coilable section configured to line a wall of the parent blood vessel and optionally to at least partially cover the orifice of the aneurysm at an external side thereof (i.e. from within/along the wall of the parent blood vessel). According to some embodiments, the first and second coilable sections may be non-braided. Advantageously, by being non-braided, the risk of perforating caused by unraveling of a braided cage formed implants is avoided. Consequently, no securing caps configured to hold together the ends of the braid are needed, allowing the coilable sections to form essentially smooth configurations without protrusions. In addition, coilable wires have a lower delivery profile as compared to braided or other implants. This since the wire requires minimal catheter lumen diameter, thereby allowing easier access to the neurovasculature. Yet another advantage is the ability to re-sheath the wire in case the operator is not satisfied with its deployment, and/or if re-deployment or exchange for a different device size is needed. Also, the time and place of detachment of the device may be accurately controlled by operating a pusher. According to some embodiments, the wire may have a diameter of below 0.65, 0.6, 0.5, 0.3, 0.15 or 0.1 mm along the length thereof. Each possibility is a separate embodiment. It is noted that although the diameters provided hereinabove are typically suitable for neurovasculature, other sizes/diameters that may be used for any other endo vascular application are also covered under the scope of this disclosure.

According to some embodiments, the first coil may be different in size and shape from the second coil. According to some embodiments, the first coil may be sized and shaped to fill the aneurysm sac. According to some embodiments, the first coil may be sized and shaped to line the aneurysm sac. According to some embodiments, the first coil may line the entire circumference of the aneurysm sac. According to some embodiments, the first coil may line approximately half of the aneurysm sac, closest to the parent vessel. According to some embodiments, the first coil may line approximately one third of the aneurysm sac, closest to the parent vessel. According to some embodiments, the first coil may be essentially ball-shaped. According to some embodiments, the first coil may have a form of a hollow ball. According to some embodiments, the first coil may be essentially bowl-shaped. According to some embodiments, the first coil may include an aperture (opening) essentially in the center thereof. According to some embodiments, the aperture may at least partially line the orifice of the vascular malformation, when in use. The aperture allows blood flow from the blood vessel to the vascular malformation (e.g., aneurism) and thus facilitates gradual healing of the vascular malformation. Gradual healing facilitated by the aperture which allows limited blood flow therethrough is preferred over a complete occlusion of the vascular malformation which typically creates an undesired abrupt hemodynamic change.

According to some embodiments, the ball shape, bowl shape or other suitable shape of the first coil may be obtained due to a pull force exerted by the second coiled section when deployed. According to some embodiments, the first section, configured to form the first coil, may have a proximal end and a distal end. According to some embodiments, the distal end of the first section may be configured to form the outermost ring of the first coil. According to some embodiments, the proximal end of the first section may be configured to form the innermost ring of the first coil. According to some embodiments, the diameter of the wire's first section may be gradually changing along a length thereof. According to some embodiments, the force exerted on a catheter (used for delivering the wire) by the wire's first section may be gradually decreasing from its proximal to its distal end. According to other embodiments, the force exerted on a catheter by the wire's first section may be gradually increasing from its proximal to its distal end. According to other embodiments, the force applied on a catheter by a distal end of the wire's first section may be weaker than the force applied on a catheter by a proximal part of the wire's first section. According to other embodiments, the force applied on a catheter by a distal end of the wire's first section may be stronger than the force applied on a catheter by a proximal part of the wire's first section. According to some embodiments, the diameter of the wire forming the first section's distal end is smaller than the diameter of the wire forming the first section's proximal part. According to other embodiments, the diameter of the wire forming the first section's distal end is larger than the diameter of the wire forming the first section's proximal part. According to some embodiments, the wire may be a tube (hollow). According to some embodiments, the first section of the tube may have variable pitch along the length thereof. This may be achieved, for example, by a plurality of cuts, such as, but not limited to, laser cuts. According to some embodiments, the plurality of cuts may be configured to reduce the force applied by the first section's distal end of the tube on a catheter. According to some embodiments, the force exerted on a catheter (delivering the wire) by the wire's first section may be decreasing from its proximal to its distal end by using a sleeve covering the proximal part/end of the wire. According to other embodiments, the force exerted on a catheter (delivering the wire) by the wire's first section may be increasing from its proximal to its distal end by using a sleeve covering the proximal part/end of the wire. According to some embodiments, the blood restricting device is formed from a wire, which is a spring/coil defining a primary wind, wherein first coil and second coil of the wire define secondary winds. The proximal section of first coil includes a core wire threaded there through. As a result, the distal part of first coil applies a lower force on the catheter than the force applied by the proximal part of first coil.

Such structure may assist in avoiding "pig-tailing" of the catheter introducing the device to the blood vessel.

According to some embodiments, the term "approximately" may refer to +/−0.5%, +/−1%, +/−2%, +/−5%, or +/−10%. Each possibility is a separate embodiment.

According to some embodiments, the second coil may be sized and shaped to alter a direction and/or a speed of blood flow there through. According to some embodiments, the second coil may be sized and shaped to cause minimal protrusion into the parent blood vessel. For example, the second coil may be sized and shaped to occupy less than 20%, less than 10%, less than 5%, less than 2% of the lumen of the parent vessel. Each possibility is a separate embodiment.

According to some embodiments, the second coil may be devoid of prongs, clips or any other protrusions, which may be thrombogenic. According to some embodiments, the second coil may be essentially flat, oval or elliptic. Each possibility is a separate embodiment. According to some embodiments, the second coil may be bowl shaped. Advantageously, the bowl shape of the second coil may enable proper engagement of the second coil with a vessel wall on both sides of an aneurysm formed at a bifurcation.

According to some embodiments, the wire forming the device may be made of a memory shape alloy material. According to some embodiments, the wire forming the device may include a memory shape alloy material. According to some embodiments, the wire forming the device may include a metal covered by a memory shape alloy material governing the shape of the metal.

According to some embodiments, the wire forming the device may be made of a super elastic material. According to some embodiments, the wire forming the device may include a super elastic material. According to some embodiments, the wire forming the device may include a metal covered by a super elastic material governing the shape of the metal. According to some embodiments, the super elastic may include platinum, nickel titanium (nitinol), tungsten or any combination thereof. Each possibility is a separate embodiment.

According, to some embodiments, the device may be configured to be delivered through a microcatheter. According to some embodiments, when deployed from the catheter, the device assumes its pre-determined configuration. According to some embodiment, the device may include, be formed, or covered with at least partially radiopaque material such as, but not limited to, tantalum, gold, tungsten or platinum, or have radiopaque markers. Each possibility is a separate embodiment. According to some embodiments, the radiopaque material may enable visualization in CT scans, X-rays and the like. According to some embodiments, the wire including the outer radio-opaque coating may have a diameter of below 0.65, 0.5, 0.45, 0.4, 0.35, 0.3 or 0.25 mm along the length thereof. Each possibility is a separate embodiment.

According to some embodiments, in its un-deployed form, within the catheter, the device may have a form of a straight wire. As used herein, the term "straight wire" may refer to a wire filament i.e. an un-winded wire, a wire with a primary wind and/or a wire with a secondary wind. According to some embodiments, the term "straight wire" may refer to the device prior to having reached its tertiary configuration, i.e. prior to deployment. It is thus understood, that during deployment the wire loops to form the first and second coils. According to some embodiments, the wire may loop into its first and second coils without requiring radial expansion.

According to some embodiments, the first coil may be configured to engage or follow the shape of the inner wall of the aneurysm sac. As used herein the term "engage" may refer to any interaction between the first coil of the device and the wall of the sac, which secures the first coil within the sac. According to some embodiments, the distal end and/or the first coil may have a circumference approximately 1%-30%, 1%-20%, 5%-20%, 5%-15%, 5%-10% or 10%-50% larger than the size and/or circumference of the aneurysm sac. Each possibility is a separate embodiment.

According to some embodiments, when the first coil of the device is deployed within the aneurysm sac, the device aligns the wall of the sac while leaving the rest of the aneurysm (e.g. its interior) unfilled. According to some embodiments, when the first coil of the device is deployed within the aneurysm sac, the device aligns part of the wall of the sac while leaving the rest of the aneurysm (e.g. the distal portion of the aneurysm sac or, in other words, farther from the parent vessel) unfilled. According to some embodiments, the size of the first coil may be adjustable. According to some embodiments, the size and shape of the first coil may be varied dependent on the type and/or size of the aneurysm to be treated. For example, to treat a relatively small berry aneurysm in cranial arteries, the first coil may be relatively small; to treat significantly larger aneurysms in larger vessels, a larger first coil may be used. According to some embodiments, the shape of the first coil may be round, oval, elliptic or any other suitable shape fitting the shape of the aneurysm sac or parts thereof. Each possibility is a separate embodiment.

According to some embodiments, the wire may further include an intermediate section formed between the first and second spiral sections. According to some embodiments, the intermediate section is configured to be deployed within and engageable with a neck of the aneurysm. According to some embodiments, the intermediate section is configured to form a bridge between the perpendicular first and second coils. According to some embodiments, the intermediate section may be coil formed. According to some embodiments, when the device is deployed within the blood vessel, the intermediate section may exert a compression force on the coil formed proximal end, thereby anchoring the proximal end to the wall of the blood vessel. Additionally or alternatively, when the device is deployed within the blood vessel, the intermediate section may exert a pulling force on the first coil, thereby opening the coil from a shape of successive rings with increasing diameters (i.e. an essentially flat structure) to a spiral with increasing diameter (i.e. an essentially bowl shaped structure). According to some embodiments, when the device is deployed within the blood vessel, the intermediate section may cause the first and second spiral sections to come closer, for example, by exerting a compression force on the first coil and/or on the second coil, thereby causing a clinging effect of the device to the vessel wall from both sides of the aneurysm.

According so some embodiments, the vertical diameter of the first, intrasaccular coil is larger than the vertical diameter of the second intraluminal coil. According so some embodiments, the horizontal diameters of the first, intrasaccular first coil and of the second intraluminal coil are larger than the horizontal diameter of the intermediate section (positionable within the aneurysm neck). According so some embodiments, the vertical diameter of the intermediate section (positionable within the aneurysm neck) is larger than the vertical diameter of the second intraluminal coil.

According to some embodiments, the first intersaccular coil, the second intraluminal coil and/or the intermediate section may be made of the same material, such as, but not limited to, platinum, tungsten or combinations thereof. Each possibility is a separate embodiment. According to some embodiments, the first intersaccular coil, the second intraluminal coil and/or the intermediate section may be made from different materials.

According to some embodiments, the device may further include a drug eluting material. According to some embodiments, the device or parts thereof, such as the first coil), the second coil and/or the intermediate section, may be coated with a drug eluting material. Each possibility is a separate embodiment. According to some embodiment, the device may include a drug eluting compartment configured to release a drug within the aneurysm, at the aneurysm neck and/or within the parent vessel in proximity to the aneurysm. Each possibility is a separate embodiment. Non-limiting examples of suitable drugs include Paclitaxel, Sirolimus and/or Everolimus. Each possibility is a separate embodiment.

Reference is now made to FIG. 1A-FIG. 1C, which schematically illustrate a non-occlusive device 100 for treating vascular malformations, in its deployed form, according to some embodiments. In its deployed form, non-occlusive device 100 is essentially a straight wire (configuration not shown), so as to fit within a microcatheter. When deployed, non-occlusive device 100 loops to form its three segments, namely first coil 110, second coil 120 having a form of a coiled plate and intermediate section 130 having a form of a spring. First coil 110 is essentially ball formed and is configured to align the wall 152 of an aneurysm sac 150 along its circumference, as shown in FIG. 1C. Second coil 120 is essentially flat and is configured to align and partially overlap a wall 162 of a parent vessel 160, so as to at least partially cover orifice 156 of aneurysm sac 150 and thereby facilitate only a restricted flow of blood into aneurysm sac 150. Intermediate section 130, interconnecting first coil 110 and second coil 120, are configured to be positioned within aneurysm neck 158 of aneurysm sac 150 and optionally to generate a clinching effect anchoring second coil 120 and first coil 110 firmly on both sides of orifice 156. It is understood that second coil 120 folds along axis 190 such that when deployed within blood vessel 160 there is essentially no or only a minimal protrusion of second coil 120 into lumen 164 of blood vessel 160. Second coil 120 may have a round shape (as shown in FIG. 1), but other shapes matching the shape of the orifice (such as but not limited to oval or elliptic shapes) are also applicable and are thus within the scope of the present disclosure. It is noted that although first coil 110 and second coil 120 are shown herein as having the same central axis 190, such that first coil 110 and second coil 120 are essentially parallel to one another, the scope of this disclosure also covers a non-occlusive device having a first coil and a second coil (similar to first coil 110 and second coil 120), which are perpendicular to one another. In other words, according to some embodiments, the central axis of the first coil may be perpendicular to the central axis of the second coil. According to additional/alternative embodiments, the central axis of the first coil and the central axis of the second coil may form any angle of between 0-90° (for example, about 20°-30°, 40°-50°, 30-60° or 60-80°).

Figure 2C:
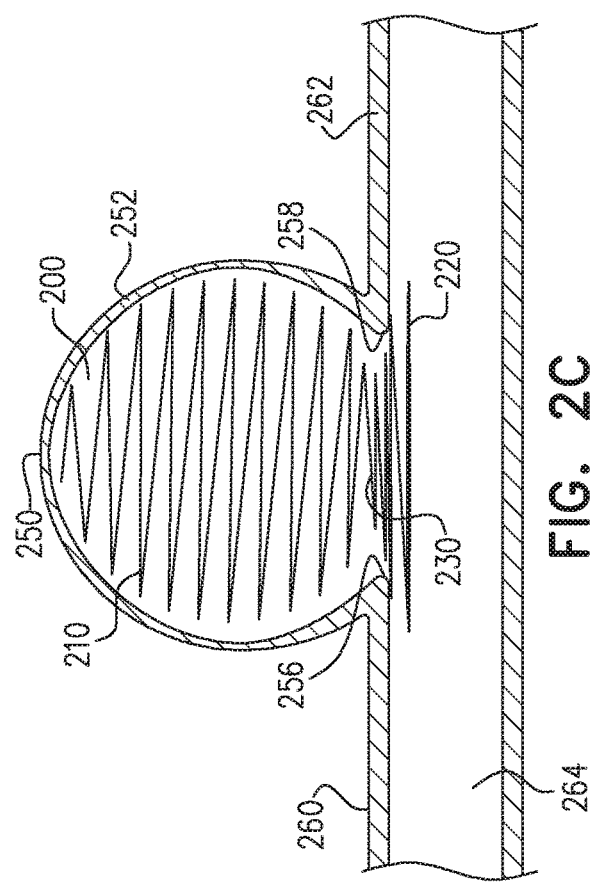
FIG. 2C schematically illustrates the non-occlusive device of FIG. 2A and FIG. 2B, deployed within a vascular malformation, according to some embodiments.
Figure 2A:
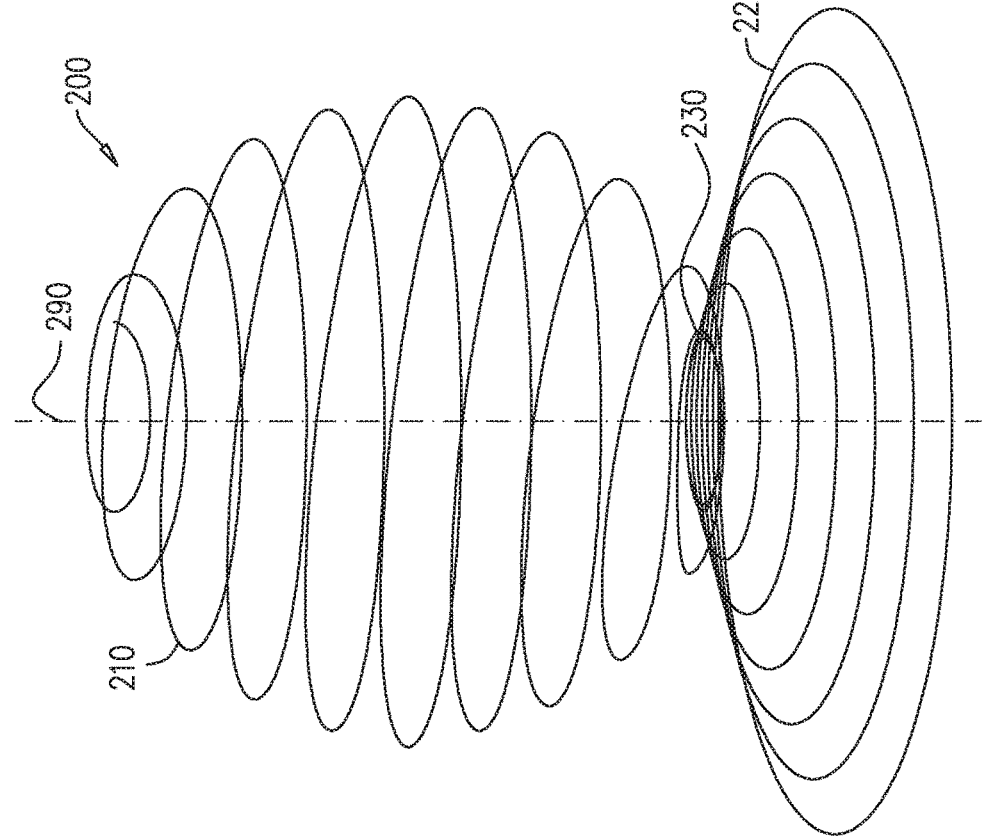

Reference is now made to FIG. 2A-FIG. 2C, which schematically illustrate a non-occlusive device 200 for treating vascular malformations, in its deployed form, according to some embodiments. In its deployed form, non-occlusive device 200 is essentially a straight wire (configuration not shown), so as to fit within a microcatheter. When deployed, non-occlusive device 200 loops to form its three segments, namely first coil 210, second coil 220 having a form of a coiled dome, intended to occupy the vertical axis of a longer neck (not shown) and intermediate section 230 having a form of a spring. First coil 210 is essentially ball formed and is configured to align the wall 252 of an aneurysm sac 250 along its circumference, as shown in FIG. 2C. Second coil 220 has a shape of a flat dome and is configured to align and partially overlap a wall 262 of a parent vessel 260, so as to at least partially cover orifice 256 of aneurysm sac 250 and thereby facilitate only a restricted flow of blood into aneurysm sac 250. Intermediate section 230, interconnecting first coil 210 and second coil 220, are configured to be positioned within aneurysm neck 258 of aneurysm sac 250 and optionally to generate a clinching effect anchoring first coil 210 and second coil 220 firmly on both sides of orifice 256. It is understood that the width of second coil 220 along axis 290 is small so that when deployed within blood vessel 260 the protrusion of second coil 220 into lumen 264 of blood vessel 260 is minimized. However, due to its dome shape, second coil 220 may cause a larger impact on the blood flow in lumen 264 of blood vessel 260 and thus on the flow of blood (direction and rate) into aneurysm sac 250, as compared to the completely flat configuration disclosed in FIG. 1A-FIG. 1C. It is noted that although first coil 210 and second coil 220 are shown herein as having the same central axis 290, such that first coil 210 and second coil 220 are essentially parallel to one another, the scope of this disclosure also covers a non-occlusive device having a first coil and a second coil (similar to first coil 210 and second coil 220), which are perpendicular to one another. In other words, according to some embodiments, the central axis of the first coil may be perpendicular to the central axis of the second coil. According to additional/alternative embodiments, the central axis of the first coil and the central axis of the second coil may form any angle of between 0-90° (for example, about 20°-30°, 40°-50°, 30-60° or 60-80°).

Figure 3B:
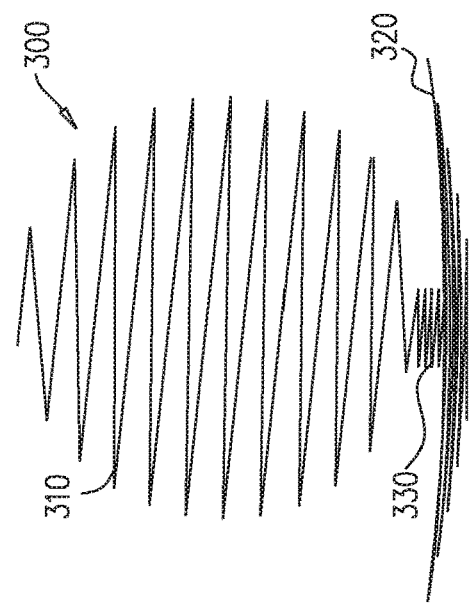
FIG. 3A-FIG. 3B schematically illustrates a non-occlusive device for treating vascular malformations, according to some embodiments.
Figure 3C:
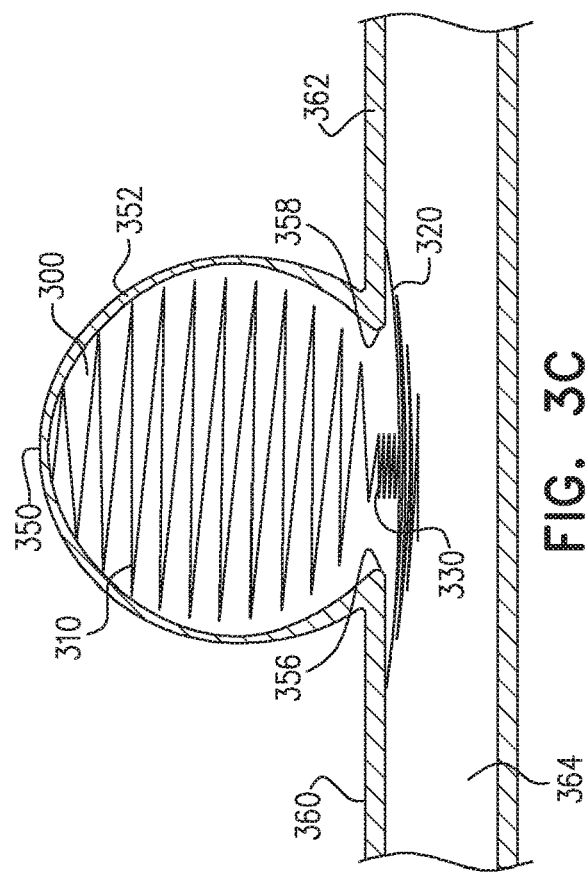
FIG. 3C schematically illustrates the non-occlusive device of FIG. 3A and FIG. 3B, deployed within a vascular malformation, according to some embodiments.
Figure 3A:
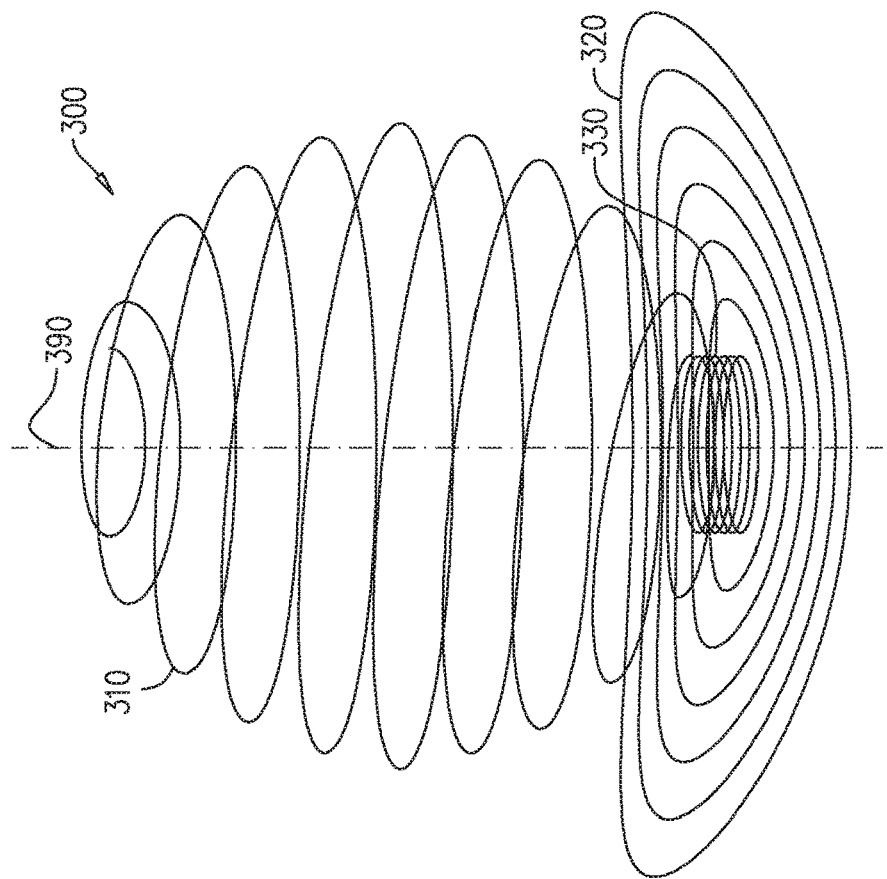

Reference is now made to FIG. 3A-FIG. 3C, which schematically illustrate a non-occlusive device 300 for treating vascular malformations, in its deployed form, according to some embodiments. In its deployed form, non-occlusive device 300 is essentially a straight wire (configuration not shown) so as to fit within a microcatheter. When deployed, non-occlusive device 300 loops to form its three segments, namely first coil 310, second coil 320 having a form of a spiraled bowl and intermediate section 330 having a form of a spring. First coil 310 is essentially ball formed and is configured to align the wall 352 of an aneurysm sac 350 along its circumference, as shown in FIG. 3C. Second coil 320 has a shape of a flat bowl and is configured to align and partially overlap a wall 362 of a parent vessel 360, so as to at least partially cover orifice 356 of aneurysm sac 350 and thereby facilitate only a restricted flow of blood into aneurysm sac 350. Intermediate section 330, interconnecting first coil 310 and second coil 320, is configured to be positioned within aneurysm neck 358 of aneurysm sac 350 and optionally to generate a clinching effect anchoring first coil 310 and second coil 320 firmly on both sides of orifice 356. It is understood that the width of second coil 320 along axis 390 is small so that when deployed within blood vessel 360, the protrusion of second coil 320 into lumen 364 of blood vessel 360 is minimized. However, due to its bowl shape, second coil 320 may cause a larger impact on the blood flow in lumen 364 of blood vessel 360 and thus on the flow of blood (direction and rate) into aneurysm sac 350, as compared to the essentially flat configuration disclosed in FIG. 1A-FIG. 1C which may almost completely inhibit the flow of blood into aneurysm sac 150. Moreover, the bowl shape of second coil 320 may be particularly suitable for restricting the flow into aneurysms located at or near bifurcations in that the sides of the bowl formed second coil 320 may engage the wall of the blood vessel on both sides of the bifurcation, as further described in FIG. 12 herein. It is noted that although first coil 310 and second coil 320 are shown herein as having the same central axis 390, such that first coil 310 and second coil 320 are essentially parallel to one another, the scope of this disclosure also covers a non-occlusive device having a first coil and a second coil (similar to first coil 310 and second coil 320), which are perpendicular to one another. In other words, according to some embodiments, the central axis of the first coil may be perpendicular to the central axis of the second coil. According to additional/alternative embodiments, the central axis of the first coil and the central axis of the second coil may form any angle of between 0-90° (for example, about 20°-30°, 40°-50°, 30-60° or 60-80°).

Figure 4B:
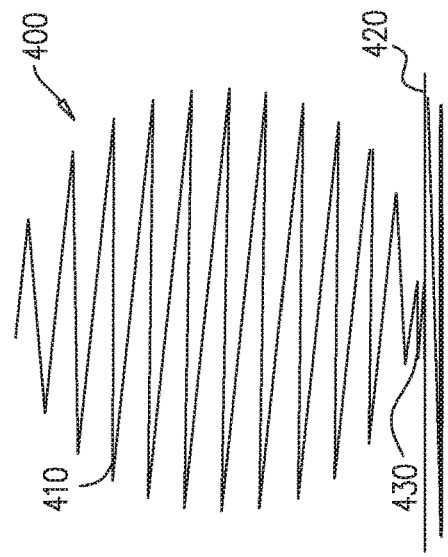
FIG. 4A-FIG. 4B schematically illustrates a non-occlusive device for treating vascular malformations, according to some embodiments.
Figure 4C:
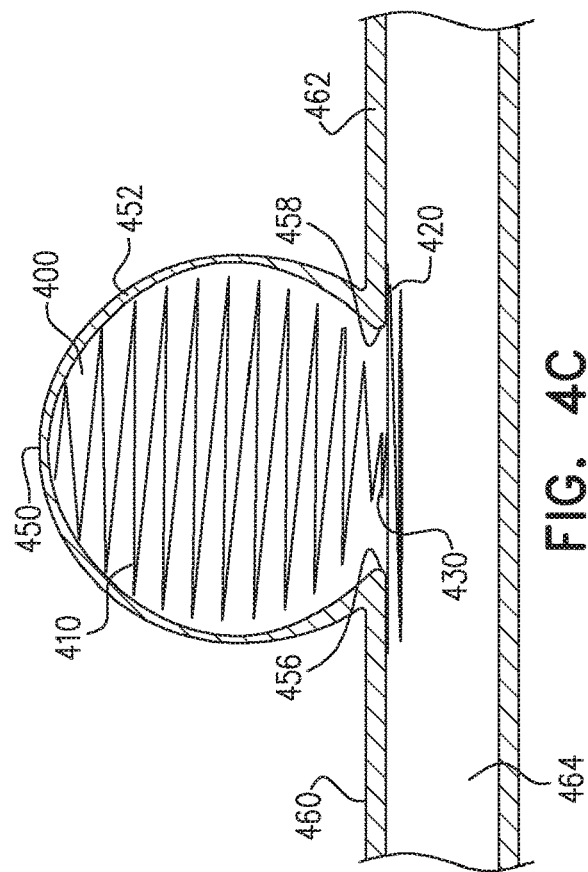
FIG. 4C schematically illustrates the non-occlusive device of FIG. 4A and FIG. 4B, deployed within a vascular malformation, according to some embodiments.
Figure 4A:
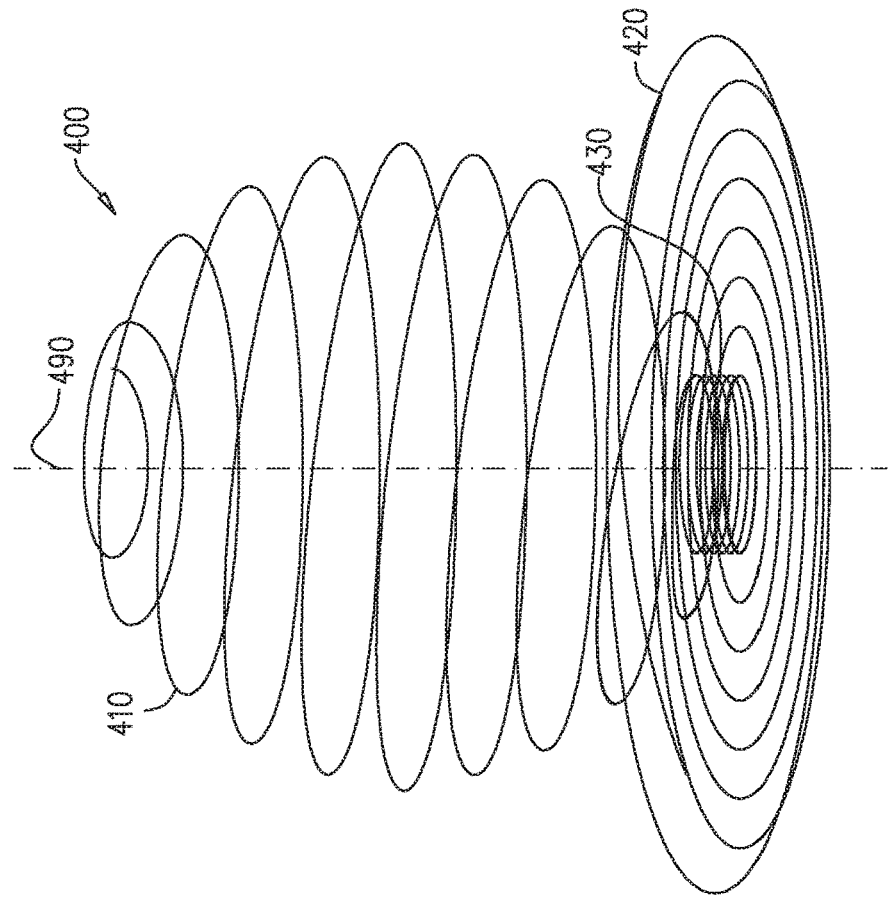

Reference is now made to FIG. 4A-FIG. 4C, which schematically illustrate a non-occlusive device 400 for treating vascular malformations, in its deployed form, according to some embodiments. In its deployed form, non-occlusive device 400 is essentially a straight wire (configuration not shown) so as to fit within a microcatheter. When deployed, non-occlusive device 400 loops to form its three segments, namely first coil 410, second coil 420 having a form of a spiraled deep plate and intermediate section 430 having a form of a spring. First coil 410 is essentially ball formed and is configured to align the wall 452 of an aneurysm sac 450 along its circumference, as shown in FIG. 4C. Second coil 420 has a shape of a flat deep plate and is configured to align and partially overlap a wall 462 of a parent vessel 460, so as to at least partially cover orifice 456 of aneurysm sac 450 and thereby facilitate only a restricted flow of blood into aneurysm sac 450. Intermediate section 430, interconnecting first coil 410 and second coil 420, are configured to be positioned within aneurysm neck 458 of aneurysm sac 450 and optionally to generate a clinching effect anchoring first coil 410 and second coil 420 firmly on both sides of orifice 456. It is understood that the width of second coil 420 along axis 490 is small so that when deployed within blood vessel 460 the protrusion of second coil 420 into lumen 464 of blood vessel 460 is smaller than that of bowl shape second coil 320, described in FIG. 3A-FIG. 3C yet larger than that of second coil 120 of FIG. 1A to FIG. 1C. As a result, a larger impact on the blood flow in lumen 464 of blood vessel 460 is obtained as compared to the completely flat configuration disclosed in FIG. 1A-FIG. 1C, yet the impact is lesser than that of bowl formed second coil 320 of FIG. 3A-FIG. 3C.

It is noted that although first coil 410 and second coil 420 are shown herein as having the same central axis 490, such that first coil 410 and second coil 420 are essentially parallel to one another, the scope of this disclosure also covers a non-occlusive device having a first coil and a second coil (similar to first coil 410 and second coil 420), which are perpendicular to one another. In other words, according to some embodiments, the central axis of the first coil may be perpendicular to the central axis of the second coil. According to additional/alternative embodiments, the central axis of the first coil and the central axis of the second coil may form any angle of between 0-90° (for example, about 20°-30°, 40°-50°, 30-60° or 60-80°).

Reference is now made to FIG. 5A-FIG. 5C, which schematically illustrate a non-occlusive device 500 for treating vascular malformations, in its deployed form, according to some embodiments. In its deployed form, non-occlusive device 500 essentially has a shape of a straight wire (configuration not shown), so as to fit within a microcatheter. When deployed, non-occlusive device 500 loops to form three segments, namely first coil 510, second coil 520 having a form of a spiraled plate (similar to second coil 120 of FIG. 1A-FIG. 1C) and intermediate section 530 having a form of a straight connecting segment. Due to its form as a straight connecting segment, the length of the wire forming intermediate section 530 is shortened, which advantageously makes its deployment easier and reduces the amount of metal introduced into the body. The spiral section of first coil 510 is essentially ball formed and is configured to align the wall 552 of an aneurysm sac 550 along its circumference, as shown in FIG. 5C. Second coil 520 is essentially flat and is configured to align and partially overlap a wall 562 of a parent vessel 560, so as to at least partially cover orifice 556 of aneurysm sac 550 and thereby facilitate only a restricted flow of blood into aneurysm sac 550. Intermediate section 530, interconnecting first coil 510 and second coil 520, are configured to be positioned within aneurysm neck 558 of aneurysm sac 550.

It is noted that although first coil 510 and second coil 520 are shown herein as having the same central axis, such that first coil 510 and second coil 520 are essentially parallel to one another, the scope of this disclosure also covers a non-occlusive device having a first coil and a second coil (similar to first coil 510 and second coil 520), which are perpendicular to one another. In other words, according to some embodiments, the central axis of the first coil may be perpendicular to the central axis of the second coil. According to additional/alternative embodiments, the central axis of the first coil and the central axis of the second coil may form any angle of between 0-90° (for example, about 20°-30°, 40°-50°, 30-60° or 60-80°).

Figure 6B:
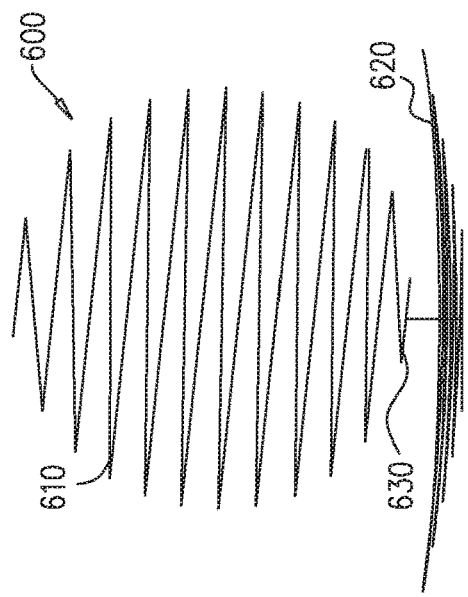
FIG. 6A-FIG. 6B schematically illustrates a non-occlusive device for treating vascular malformations, according to some embodiments.
Figure 6C:
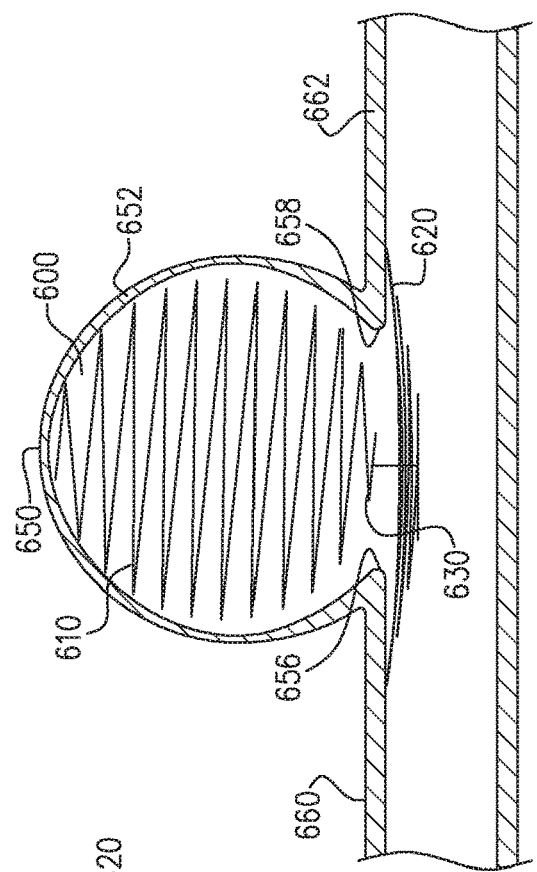
FIG. 6C schematically illustrates the non-occlusive device of FIG. 6A and FIG. 6B, deployed within a vascular malformation, according to some embodiments.
Figure 6A:
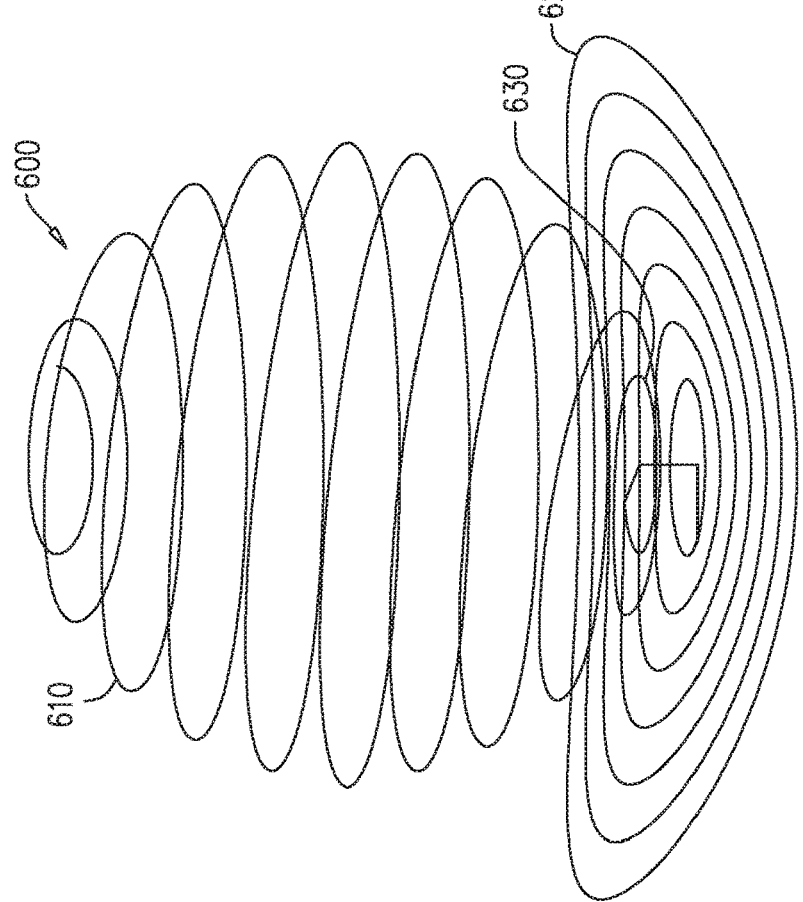

Reference is now made to FIG. 6A-FIG. 6C, which schematically illustrate a non-occlusive device 600 for treating vascular malformations, in its deployed form, according to some embodiments. In its deployed form, non-occlusive device 600 is essentially a straight wire (configuration not shown), so as to fit within a microcatheter. When deployed, non-occlusive device 600 loops to form its three segments, namely first coil 610, second coil 620 having a form of a spiraled bowl (similarly to second coil 320 of FIG. 3A-FIG. 3C) and intermediate section 630, having a form of a straight connecting segment. First coil 610 is essentially ball formed and is configured to align the wall 652 of an aneurysm sac 650 along its circumference, as shown in FIG. 6C. Second coil 620 has a shape of a flat bowl and is configured to align and partially overlap a wall 662 of a parent vessel 660, so as to at least partially cover orifice 656 of aneurysm sac 650 and thereby facilitate only a restricted flow of blood into aneurysm sac 650. Intermediate section 630, interconnecting first coil 610 and second coil 620, configured to be positioned within aneurysm neck 658 of aneurysm sac 650. It is noted that although first coil 610 and second coil 620 are shown herein as having the same central axis, such that first coil 610 and second coil 620 are essentially parallel to one another, the scope of this disclosure also covers a non-occlusive device having a first coil and a second coil (similar to first coil 610 and second coil 620), which are perpendicular to one another. In other words, according to some embodiments, the central axis of the first coil may be perpendicular to the central axis of the second coil. According to additional/alternative embodiments, the central axis of the first coil and the central axis of the second coil may form any angle of between 0-90° (for example, about 20°-30°, 40°-50°, 30-60° or 60-80°).

Figure 7B:
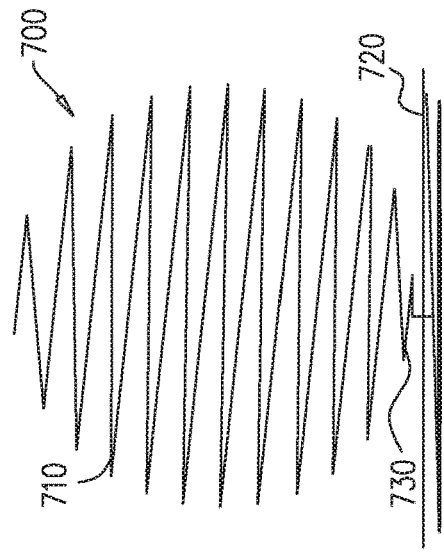
FIG. 7A-FIG. 7B schematically illustrates a non-occlusive device for treating vascular malformations, according to some embodiments.
Figure 7C:
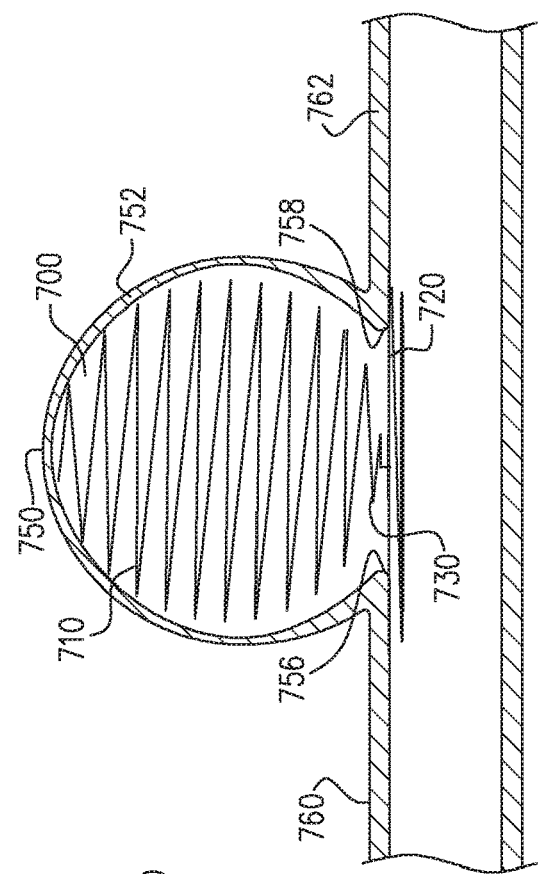
FIG. 7C schematically illustrates the non-occlusive device of FIG. 7A and FIG. 7B, deployed within a vascular malformation, according to some embodiments.
Figure 7A:
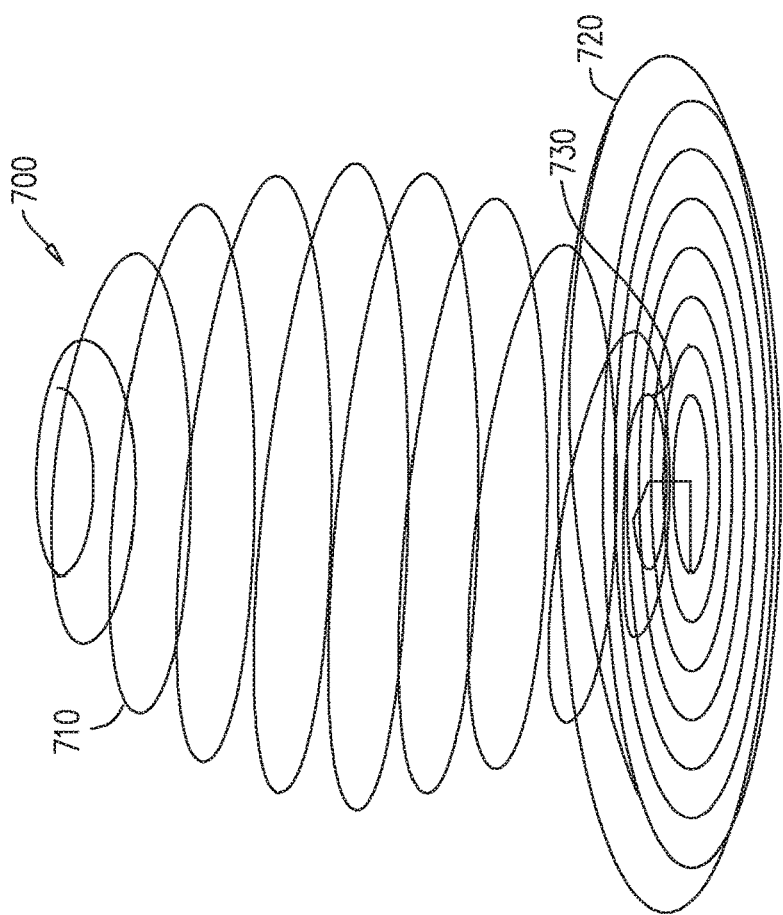

Reference is now made to FIG. 7A-FIG. 7C, which schematically illustrate a non-occlusive device 700 for treating vascular malformations, in its deployed form, according to some embodiments. In its deployed form, non-occlusive device 700 is essentially a straight wire (configuration not shown), so as to fit within a microcatheter. When deployed, non-occlusive device 700 loops to form its three segments, namely first coil 710, second coil 720 having a form of a spiraled deep plate (similar to second coil 420 of FIG. 4A-FIG. 4C) and intermediate section 730 having a form of a straight connecting segment. First coil 710 is essentially ball formed and is configured to align the wall 752 of an aneurysm sac 750 along its circumference, as shown in FIG. 7C. Second coil 720 has a shape of a flat deep plate and is configured to align and partially overlap a wall 762 of a parent vessel 760, so as to at least partially cover orifice 756 of aneurysm sac 750 and thereby facilitate only a restricted flow of blood into aneurysm sac 750. Intermediate section 730, interconnecting first coil 710 and second coil 720, are configured to be positioned within aneurysm neck 758 of aneurysm sac 750.

It is noted that although first coil 710 and second coil 720 are shown herein as having the same central axis, such that first coil 710 and second coil 720 are essentially parallel to one another, the scope of this disclosure also covers a non-occlusive device having a first coil and a second coil (similar to first coil 710 and second coil 720), which are perpendicular to one another. According to additional/alternative embodiments, the central axis of the first coil and the central axis of the second coil may form any angle of between 0-90° (for example, about 20°-30°, 40°-50°, 30-60° or 60-80°).

Reference is now made to FIG. 8A-FIG. 8C, which schematically illustrate a non-occlusive device 800 for treating vascular malformations, in its deployed form, according to some embodiments. In its deployed form, non-occlusive device 800 is essentially a straight wire (configuration not shown) so as to fit within a microcatheter. When deployed, non-occlusive device 800 loops to form its three segments, namely first coil 810, second coil 820 having a form of a spiraled plate (similar to second coil 120 of FIG. 1A-FIG. 1C) and intermediate section 830 having a form of a spring. First coil 810 has a shape of a deep bowl and is configured to align the part of wall 852 of an aneurysm sac 850 closest to parent vessel 860, as shown in FIG. 8C. Due to the fact that first coil 810 only aligns part of wall 852 of aneurism sac 850, the length of the wire forming first coil 810 is shortened, which advantageously makes its deployment easier and reduces the amount of metal introduced into the body. Second coil 820 is essentially flat and is configured to align and partially overlap a wall 862 of parent vessel 860, so as to at least partially cover orifice 856 of aneurysm sac 850 and thereby facilitate only a restricted flow of blood into aneurysm sac 850. Intermediate section 830, interconnecting first coil 810 and second coil 820, are configured to be positioned within aneurysm neck 858 of aneurysm sac 850 and optionally to generate a clinching effect anchoring first coil 810 and second coil 820 firmly on both sides of orifice 856.

It is noted that although first coil 810 and second coil 820 are shown herein as having the same central axis, such that first coil 810 and second coil 820 are essentially parallel to one another, the scope of this disclosure also covers a non-occlusive device having a first coil and a second coil (similar to first coil 810 and second coil 820), which are perpendicular to one another. In other words, according to some embodiments, the central axis of the first coil may be perpendicular to the central axis of the second coil. According to additional/alternative embodiments, the central axis of the first coil and the central axis of the second coil may form any angle of between 0-90° (for example, about 20°-30°, 40°-50°, 30-60° or 60-80°).

Figure 9B:
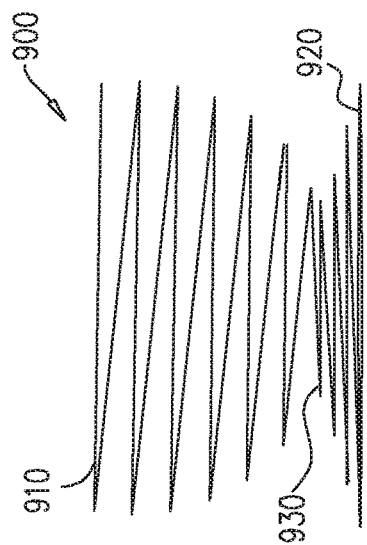
FIG. 9A-FIG. 9B schematically illustrates a non-occlusive device for treating vascular malformations, according to some embodiments.
Figure 9C:
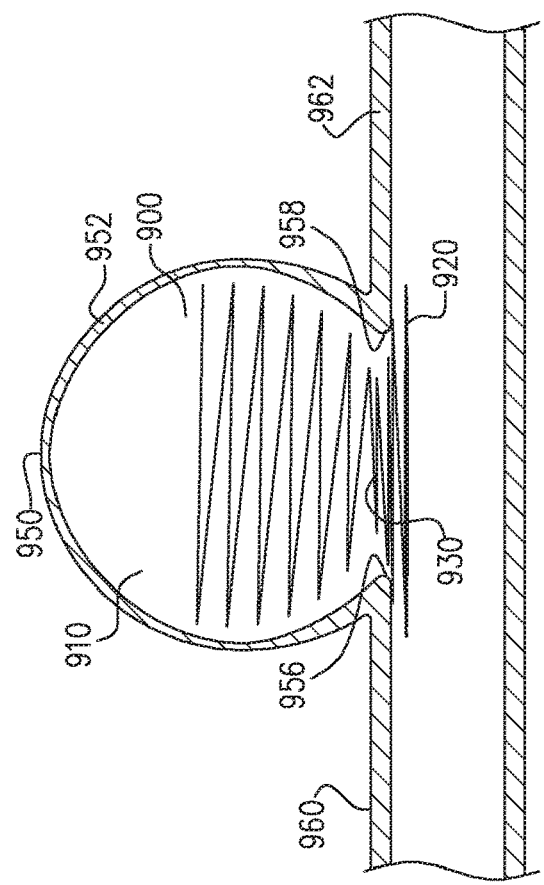
FIG. 9C schematically illustrates the non-occlusive device of FIG. 9A and FIG. 9B, deployed within a vascular malformation, according to some embodiments.
Figure 9A:
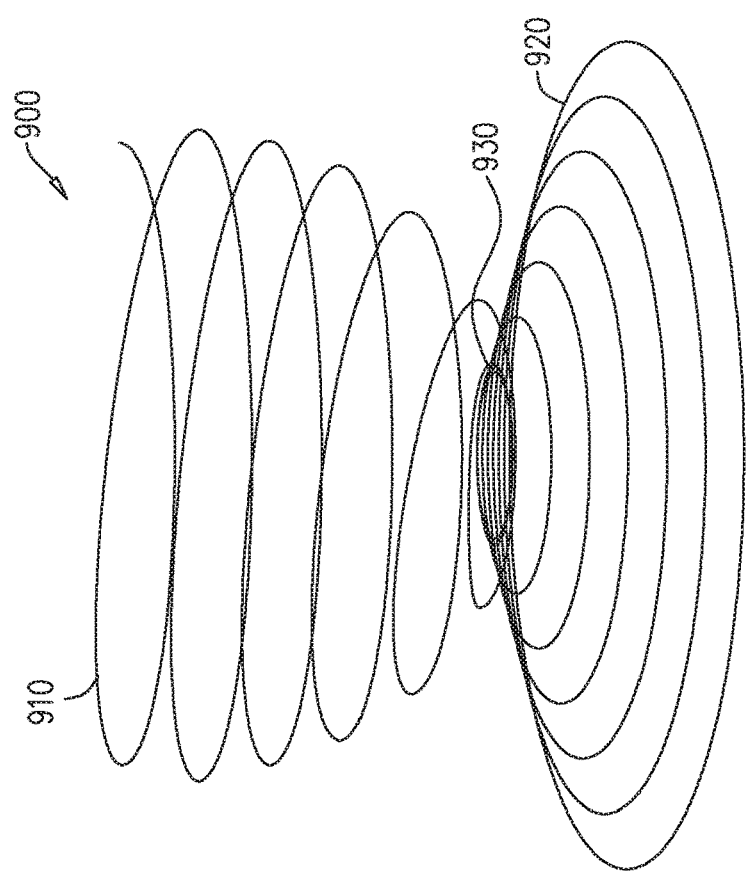

Reference is now made to FIG. 9A-FIG. 9C, which schematically illustrate a non-occlusive device 900 for treating vascular malformations, in its deployed form, according to some embodiments. In its deployed form, non-occlusive device 900 is essentially a straight wire (configuration not shown), so as to fit within a microcatheter. When deployed, non-occlusive device 900 loops to form its three segments, namely first coil 910, second coil 920 having a form of a spiraled dome (similar to second coil 220 of FIG. 2A-FIG. 2C) and intermediate section 930 having a form of a spring. First coil 910 has a shape of a deep bowl and is configured to align the part of wall 952 of an aneurysm sac 950 closest to parent vessel 960, as shown in FIG. 9C. Due to the fact that first coil 910 only aligns part of wall 952 of aneurism sac 950, the length of the wire forming first coil 910 is shortened, which advantageously makes its deployment easier and reduces the amount of metal introduced into the body. Second coil 920 has a shape of a flat dome and is configured to align and partially overlap a wall 962 of a parent vessel 960, so as to at least partially cover orifice 956 of aneurysm sac 950 and thereby facilitate only a restricted flow of blood into aneurysm sac 950. Intermediate section 930, interconnecting first coil 910 and second coil 920, are configured to be positioned within aneurysm neck 958 of aneurysm sac 950 and optionally to generate a clinching effect anchoring first coil 910 and second coil 920 firmly on both sides of orifice 956.

It is noted that although first coil 910 and second coil 920 are shown herein as having the same central axis, such that first coil 910 and second coil 920 are essentially parallel to one another, the scope of this disclosure also covers a non-occlusive device having a first coil and a second coil (similar to first coil 910 and second coil 920), which are perpendicular to one another. According to additional/alternative embodiments, the central axis of the first coil and the central axis of the second coil may form any angle of between 0-90° (for example, about 20°-30°, 40°-50°, 30-60° or 60-80°).

Figure 10B:
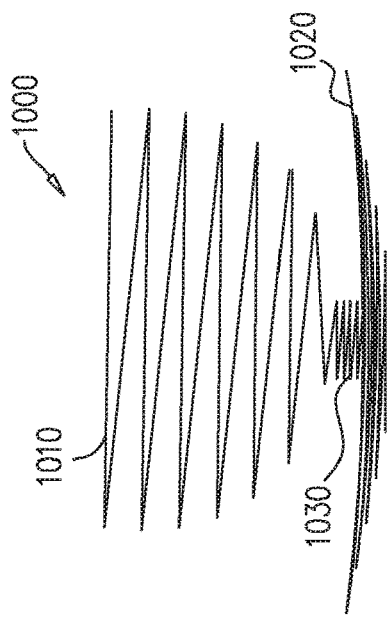
FIG. 10A-FIG. 10B schematically illustrates a non-occlusive device for treating vascular malformations, according to some embodiments.
Figure 10C:
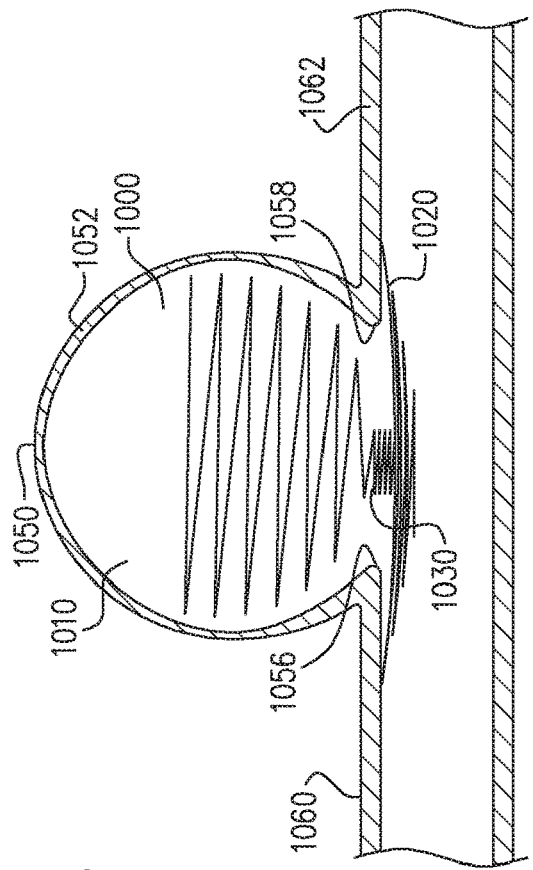
FIG. 10C schematically illustrates the non-occlusive device of FIG. 10A and FIG. 10B, deployed within a vascular malformation, according to some embodiments.
Figure 10A:
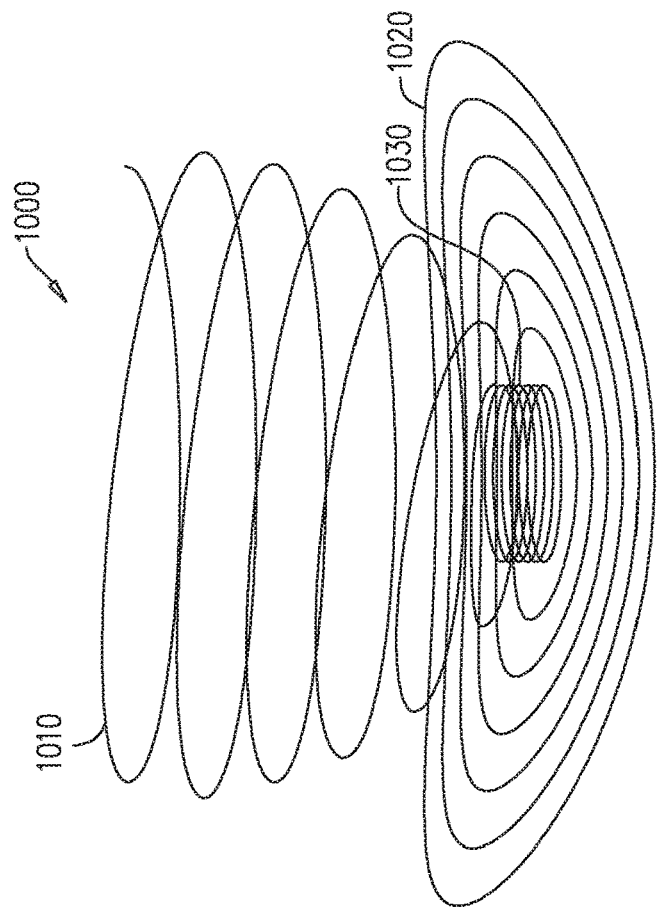

Reference is now made to FIG. 10A-FIG. 10C, which schematically illustrate a non-occlusive device 1000 for treating vascular malformations, in its deployed form, according to some embodiments. In its deployed form, non-occlusive device 1000 is essentially a straight wire (configuration not shown), so as to fit within a microcatheter. When deployed, non-occlusive device 1000 loops to form its three segments, namely first coil 1010, second coil 1020 having a form of a spiraled bowl (similarly to second coil 320 of FIG. 3A-FIG. 3C) and intermediate section 1030 having a form of a spring. First coil 1010 has a shape of a deep bowl and is configured to align the part of wall 1052 of an aneurysm sac 1050 closest to parent vessel 1060, as shown in FIG. 10C. Due to the fact that first coil 1010 only aligns part of wall 1052 of aneurysm sac 1050, the length of the wire forming first coil 1010 is shortened, which advantageously makes its deployment easier and reduces the amount of metal introduced into the body. Second coil 1020 has a shape of a flat bowl and is configured to align and partially overlap a wall 1062 of a parent vessel 1060, so as to at least partially cover orifice 1056 of aneurysm sac 1050 and thereby facilitate only a restricted flow of blood into aneurysm sac 1050. Intermediate section 1030, interconnecting first coil 1010 and second coil 1020, are configured to be positioned within aneurysm neck 1058 of aneurysm sac 1050 and optionally to generate a clinching effect anchoring first coil 1010 and second coil 1020 firmly on both sides of orifice 1056. It is noted that although first coil 1010 and second coil 1020 are shown herein as having the same central axis, such that first coil 1010 and second coil 1020 are essentially parallel to one another, the scope of this disclosure also covers a non-occlusive device having a first coil and a second coil (similar to first coil 1010 and second coil 1020), which are perpendicular to one another. In other words, according to some embodiments, the central axis of the first coil may be perpendicular to the central axis of the second coil. According to additional/alternative embodiments, the central axis of the first coil and the central axis of the second coil may form any angle of between 0-90° (for example, about 20°-30°, 40°-50°, 30-60° or 60-80°).

Reference is now made to FIG. 11A-FIG. 1C, which schematically illustrate a non-occlusive device 1100 for treating vascular malformations, in its deployed form, according to some embodiments. In its deployed form, non-occlusive device 1100 is essentially a straight wire (configuration not shown), so as to fit within a microcatheter. When deployed, non-occlusive device 1100 loops to form its three segments, namely first coil 1110, second coil 1120 having a form of a spiraled deep plate (similarly to second coil 420 of FIG. 4A-FIG. 4C) and intermediate section 1130 having a form of a spring. First coil 1110 has a shape of a deep bowl and is configured to align the part of wall 1152 of an aneurysm sac 1150 closest to parent vessel 1160, as shown in FIG. 11C. Due to the fact that first coil 1110 only aligns part of wall 1152 of aneurysm sac 1150, the length of the wire forming first coil 1110 is shortened, which advantageously makes its deployment easier and reduces the amount of metal introduced into the body. Second coil 1120 has a shape of a flat deep plate and is configured to align and partially overlap a wall 1162 of a parent vessel 1160, so as to at least partially cover orifice 1156 of aneurysm sac 1150 and thereby facilitate only a restricted flow of blood into aneurysm sac 1150. Intermediate section 1130, interconnecting first coil 1110 and second coil 1120, are configured to be positioned within aneurysm neck 1158 of aneurysm sac 1150 and optionally to generate a clinching effect anchoring first coil 1120 and second coil 1110 firmly on both sides of orifice 1156.

It is noted that although first coil 1110 and second coil 1120 are shown herein as having the same central axis, such that first coil 1110 and second coil 1120 are essentially parallel to one another, the scope of this disclosure also covers a non-occlusive device having a first coil and a second coil (similar to first coil 1110 and second coil 1120), which are perpendicular to one another. In other words, according to some embodiments, the central axis of the first coil may be perpendicular to the central axis of the second coil. According to additional/alternative embodiments, the central axis of the first coil and the central axis of the second coil may form any angle of between 0-90° (for example, about 20°-30°, 40°-50°, 30-60° or 60-80°).

Figure 12:
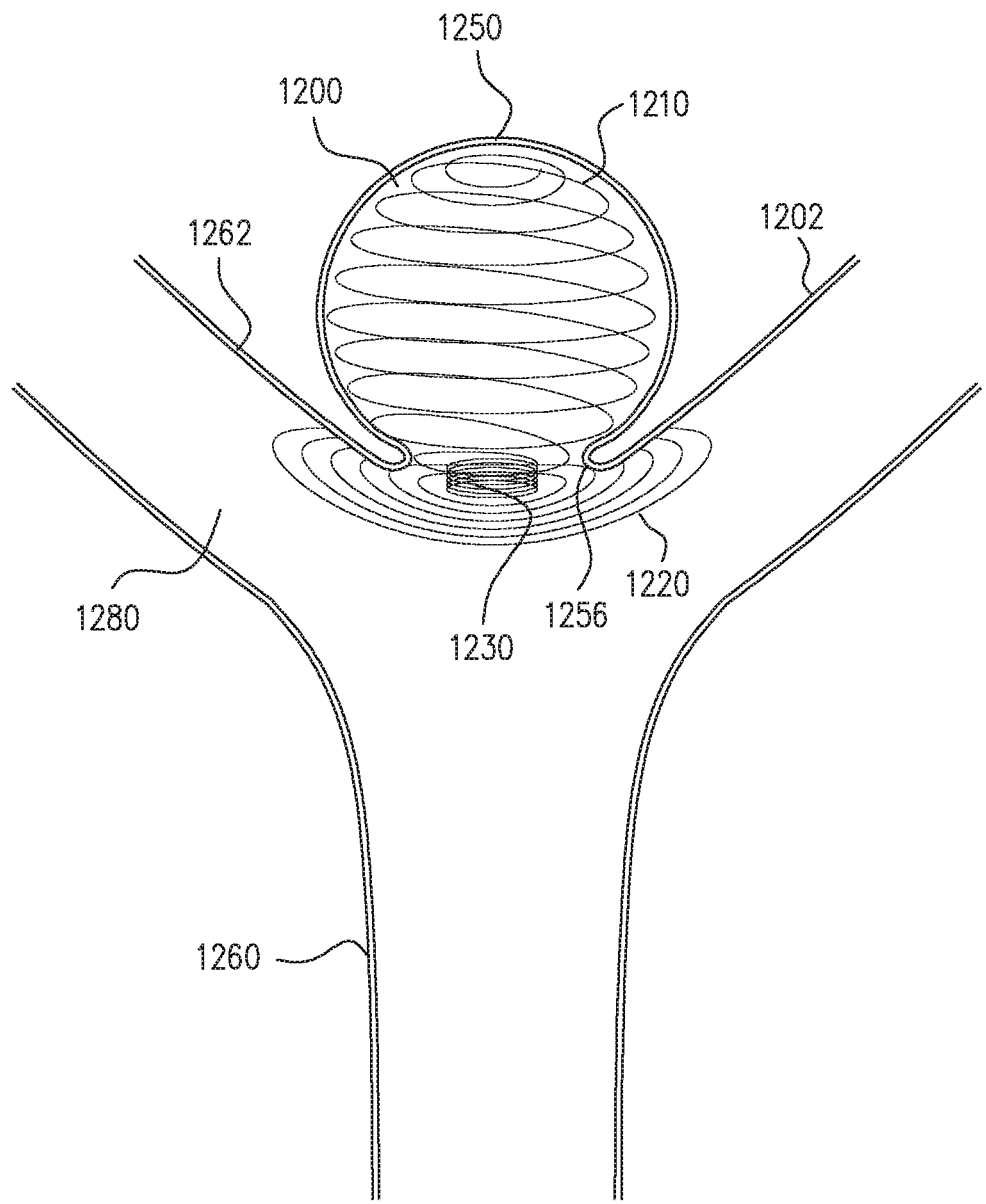
FIG. 12 schematically illustrates a non-occlusive device deployed within a vascular malformation at a bifurcation, according to some embodiments.

Reference is now made to FIG. 12, which schematically illustrate a non-occlusive device 1200 deployed within a vascular malformation 1250 at a bifurcation 1280 of a blood vessel 1260, according to some embodiments. Non-occlusive device 1200 has three segments, namely first coil 1210, second coil 1220 having a form of a spiraled bowl (as essentially shown in FIG. 3A-FIG. 3C herein) and intermediate section 1230 having a form of a spring. Advantageously, the bowl shape of second coil 1220 enables the alignment of second coil 1220 along part of wall 1262 on both sides of bifurcation 1280 of blood vessel 1260. This, on the one hand, facilitates covering orifice 1256 of aneurysm sac 1250, and on the other hand, firm anchoring to wall 1262 and wall 1202 on both sides of bifurcation 1280, consequently permitting a restricted flow of blood to enter aneurysm sac 1250. It is noted that although first coil 1210 and second coil 1220 are shown herein as having the same central axis, such that first coil 1210 and second coil 1220 are essentially parallel to one another, the scope of this disclosure also covers a non-occlusive device having a first coil and a second coil (similar to first coil 1210 and second coil 1220), which are perpendicular to one another. In other words, according to some embodiments, the central axis of the first coil may be perpendicular to the central axis of the second coil. According to additional/alternative embodiments, the central axis of the first coil and the central axis of the second coil may form any angle of between 0-90° (for example, about 20°-30°, 40°-50°, 30-60° or 60-80°). According to some embodiments, a second coil may be positioned in only one branch of the bifurcation and thus be anchored to wall 1262 or to wall 1202.

Figure 13A:
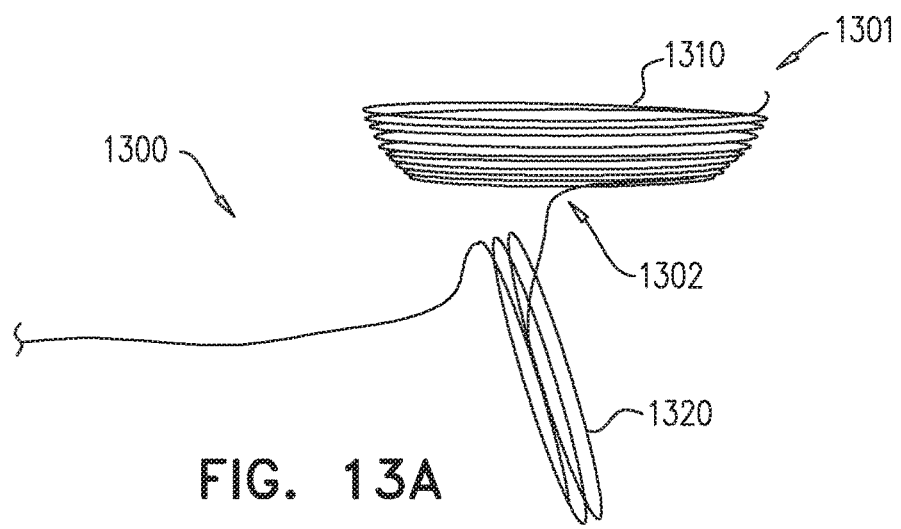
FIG. 13A illustrates a blood restricting device for treating vascular malformations, according to some embodiments.
Figure 13B:
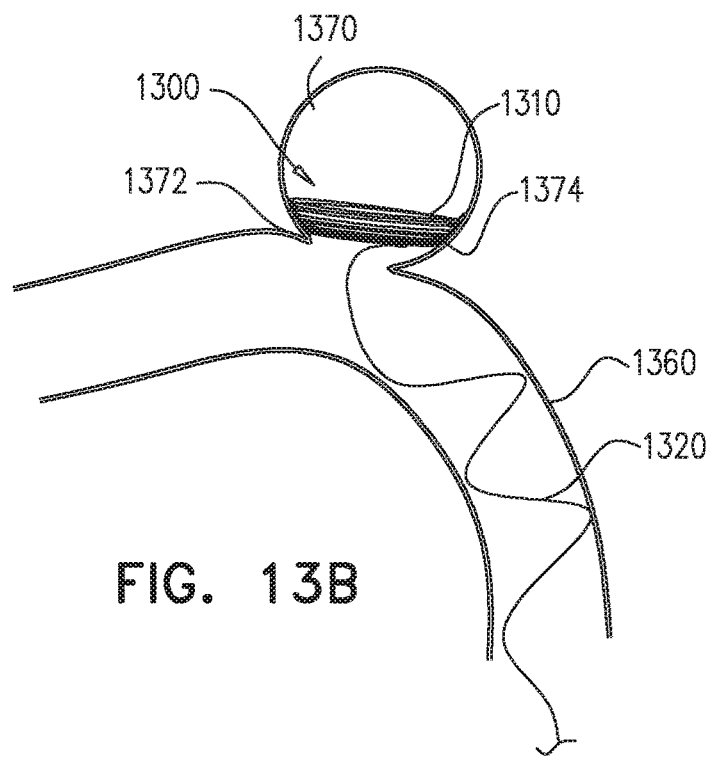
FIG. 13B illustrates the non-occlusive device of FIG. 13A deployed within a vascular malformation, according to some embodiments.
Figure 13C:
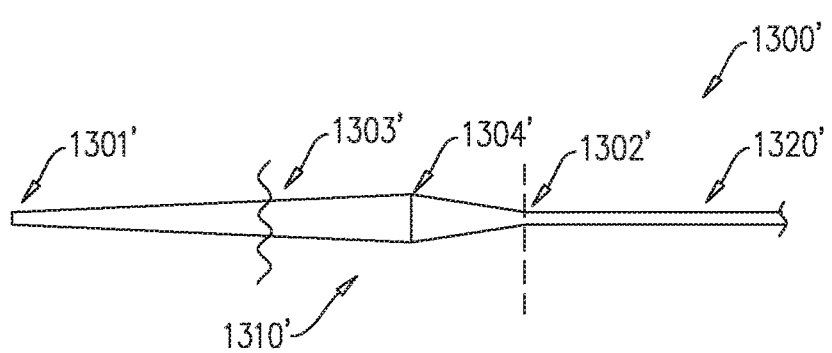
FIG. 13C illustrates a magnified view of an optional shape of a wire forming the blood restricting device of FIG. 13A, according to some embodiments.

Reference is now made to FIGS. 13A-13C. FIG. 13A illustrates a blood restricting device 1300 for treating vascular malformations in its non-restricted form, according to some embodiments. FIG. 13B shows blood restricting device 1300 deployed within a blood vessel 1360 with a vascular deformation 1370. In its restricted form, blood restricting device 1300 is essentially a straight wire (configuration not shown), so as to fit within a microcatheter. Blood restricting device 1300 has two sections, which when deployed, loops to form a first coil 1310, and a second coil 1320. First coil 1310 has a form of a bowl and is essentially perpendicular to second coil 1320. First coil 1310 is configured to align the neck 1372 of vascular malformation 1370 and/or part of the wall 1374 of vascular malformation 1370 closest to neck 1372, as shown in FIG. 13B. Second coil 1320 forms a looped spiral aligning an inner wall of a blood vessel 1360.

As shown in FIG. 13A, first coil 1310 has a distal end 1301 (which is configured to be inserted into to the blood vessel first) and a proximal end 1302 which also contiguously forms a distal end of second coil 1320 with or without an intermediate section, as shown hereinabove according to some embodiments.

FIG. 13C illustrates a magnified view of an optional shape of a wire forming the non-occlusive blood restricting device of FIG. 13A, according to some embodiments. The wire forming blood restricting device 1300 may have, according to some embodiments, various shapes or forms. According to some embodiments, such shapes/forms may affect the force each section of the wire applies of a catheter used to deliver the device into the blood vessel. For example, it is sometimes desired that the distal part of the device (which is inserted to the blood vessel first) will apply a lower force on the catheter than the force applied by a proximal section in order to avoid "pig-tailing" of the catheter and in order to facilitate the insertion of the device into the target location. This may be achieved, for example, by a wire 1300' forming a blood restricting device, such as blood restricting device 1300. Wire 1300', shown in a straight, stretched configuration, has a first section 1310' (similar to first coil 1310 of FIG. 3A) having a distal end 1301' (similar to distal end 1301 of FIG. 3A) and a proximal end 1302' (similar to distal end 1302 of FIG. 3A) which contiguously forms a distal end of second section 1320' (similar to second coil 1320 of FIG. 3A). The diameter of distal end 1301' is smaller than a diameter of a proximal section 1303', forming a tapered shape. According to some optional embodiments, the diameter reaches a maximal value at section 1304' (located between proximal section 1303' and a proximal end 1302') and then reduces to form second coil 1320' (similar to second coil 1320 of FIG. 3A).

Figure 14:
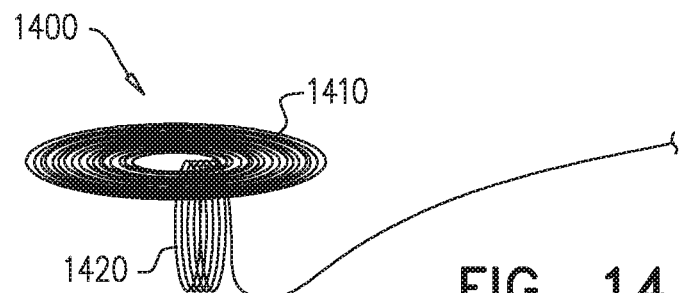
FIG. 14 illustrates a blood restricting device for treating vascular malformations, according to some embodiments.

FIG. 14 illustrates a blood restricting device 1400 for treating vascular malformations in its deployed form, according to some embodiments. In its restricted form, blood restricting device 1400 is essentially a straight wire (configuration not shown), so as to fit within a microcatheter. Blood restricting device 1400 has two sections, which when deployed, loops to form a first coil 1410, and a second coil 1420. First coil 1410 has a form of a flat plate, which is essentially perpendicular to second coil 1420. First coil 1410 is configured to obtain a bowl shape once deployed within the vascular malformations and/or upon application of a pull force thereon. First coil 1410 is configured to align a neck of a vascular malfunction and/or part of the wall of the vascular malfunction closest to neck. Second coil 1420 forms a loop circumferentially lining the wall of the blood vessel. First coil 1410 may also be configured to obtain shapes other than a bowl shape.

Figure 15:
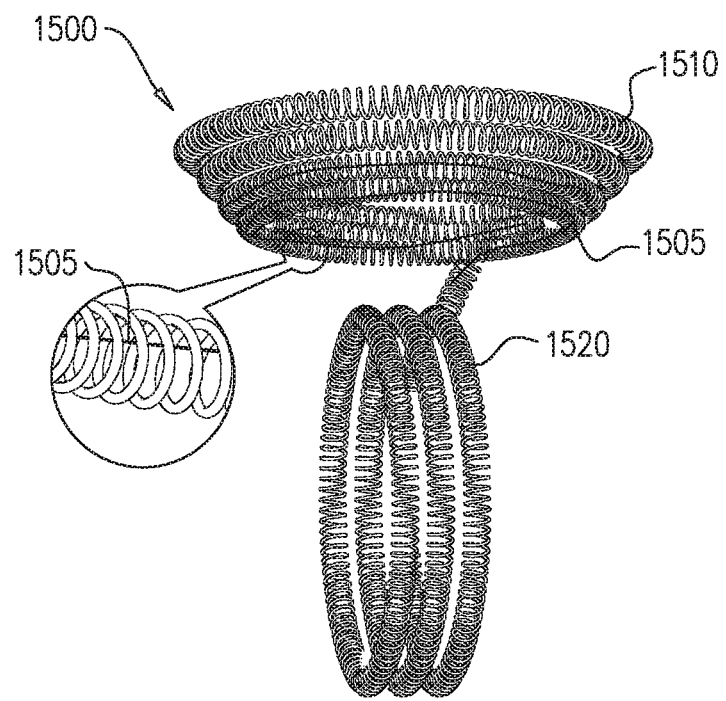
FIG. 15 illustrates a blood restricting device for treating vascular malformations, according to some embodiments.

FIG. 15 illustrates a blood restricting device 1500 for treating vascular malformations, according to some embodiments. Blood restricting device 1500 has two sections, which when deployed, loop to form a first coil 1510, and a second coil 1520. First coil 1510 has a form of a bowl and is essentially perpendicular to second coil 1520. First coil 1510 is configured to align the neck of vascular malfunction and/or part of the wall of vascular malfunction closest to neck (not shown). Second coil 1520 forms a looped spiral aligning a wall of a blood vessel (not shown). Blood restricting device 1500 is formed from a wire, which is a spring/coil defining a primary wind, wherein first coil 1510 and second coil 1520 of the wire define secondary winds. It is noted that second coil 1520 may also be formed from a wire without the primary wind. A proximal section of first coil 1510 includes a core wire 1505 threaded there through. As a result, the distal part of first coil 1510 is configured to apply a lower force on the catheter than the force applied by the proximal part of first coil 1510. This structure may also assist in avoiding "pig-tailing" of the catheter introducing the device to the blood vessel.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A non-occlusive blood-restricting device for use with a microcatheter and for treating a vascular malformation, the blood-restricting device comprising:
   a first section configured to assume a first shape when deployed from the microcatheter within a portion of the vascular malformation so as to at least partially cover an orifice of the vascular malformation, the portion of the vascular malformation including one or more anatomical features selected from the group consisting of: a neck of the vascular malformation and a wall of the vascular malformation, wherein the first shape defines a sequence of loops having a gradually decreasing diameter and coaxial around a first central axis;
   a second section configured to assume a second shape when deployed from the microcatheter, wherein the second shape defines a sequence of one or more loops having a constant or gradually decreasing diameter around a second central axis; and
   an intermediate section, which connects the first and the second sections and is configured to space apart the first and the second sections when deployed from the microcatheter,
   wherein the first central axis of the first shape is coaxial with or essentially parallel to the second central axis of the second shape when the blood-restricting device is not restrained.

2. The device according to claim 1, wherein the intermediate section is shaped as a straight connecting segment.

3. The device according to claim 1, wherein the intermediate section is helical when the blood-restricting device is not restrained.

4. The device according to claim 3, wherein the helical intermediate section has a constant diameter when the blood-restricting device is not restrained.

5. The device according to claim 1, wherein the first central axis is coaxial with the second central axis when the blood-restricting device is not restrained.

6. The device according to claim 1, wherein the second shape defines a single loop when the blood-restricting device is not restrained.

7. The device according to claim 1, wherein the blood-restricting device comprises a wire, and wherein the first section, second section, and intermediate section are formed from the wire.

8. The device according to claim 1, wherein the first shape has a form of a bowl when the blood-restricting device is not restrained.

9. The device according to claim 1, wherein the first shape has a form of a flat plate when the blood-restricting device is not restrained.

10. The device according to claim 1, wherein the first section and the second section comprise a memory shape alloy.

11. The device according to claim 1, wherein the first section and the second sections comprise a superelastic alloy.

12. The device according to claim 1, wherein a vertical diameter of the first shape is greater than a vertical diameter of the second shape when the blood-restricting device is not restrained.

13. The device according to claim 1, wherein the blood-restricting device comprises a wire, wherein the first shape is defined by the wire, and wherein a diameter of the wire at a distal end of the first shape is larger than a diameter of the wire at a proximal part of the first shape, such that the wire has a tapered shape at the first section thereof.

14. The device according to claim 1, wherein the first shape is shaped so as to define an aperture essentially in a center thereof, the aperture configured to at least partially line the orifice of the vascular malformation when the first shape is deployed from the microcatheter.

15. A kit comprising the blood-restricting device according to claim 1, the kit further comprising the microcatheter.

16. The device according to claim 1, wherein the first central axis is essentially parallel to the second central axis when the blood-restricting device is not restrained.

17. The device according to claim 1, wherein the second shape defines a sequence of loops coaxial around the second central axis when the blood-restricting device is not restrained.

18. The device according to claim 17, wherein the loops of the second shape have a generally constant diameter when the blood-restricting device is not restrained.

19. A method for treating a vascular malformation, the method comprising:
providing a non-occlusive blood-restricting device for treating a vascular malformation, the blood-restricting device including:
(a) a first section configured to assume a first shape when deployed from a microcatheter within a portion of the vascular malformation so as to at least partially cover an orifice of the vascular malformation, the portion of the vascular malformation including one or more anatomical features selected from the group consisting of: a neck of the vascular malformation and a wall of the vascular malformation, wherein the first shape defines a sequence of loops having a gradually decreasing diameter and coaxial around a first central axis;
(b) a second section configured to assume a second shape when deployed from the microcatheter, wherein the second shape defines a sequence of one or more loops having a constant or gradually decreasing diameter around a second central axis; and
(c) an intermediate section, which connects the first and the second sections and is configured to space apart the first and the second sections when deployed from the microcatheter;
inserting, using the microcatheter, the non-occlusive blood-restricting device into the blood vessel; and
deploying the first section, the second section, and the intermediate section from the microcatheter such that the first section at least partially covers the orifice of the vascular malformation and the intermediate section spaces apart the first and the second sections, and the first central axis of the first shape is coaxial with or essentially parallel to the second central axis of the second shape.

* * * * *